United States Patent [19]

Barker et al.

[11] Patent Number: 5,384,309
[45] Date of Patent: Jan. 24, 1995

[54] CYCLIZED PEPTIDES AND THEIR USE AS PLATELET AGGREGATION INHIBITORS

[75] Inventors: Peter L. Barker, El Granada; John P. Burnier, Pacifica; Eugene D. Thorsett, Moss Beach, all of Calif.

[73] Assignee: Genentech, Inc., San Francisco, Calif.

[21] Appl. No.: 380,957

[22] Filed: Jul. 17, 1989

[51] Int. Cl.$^6$ .................. A61K 37/00; A61K 37/02; C07K 5/00; C07K 7/00
[52] U.S. Cl. ........................... 514/11; 530/317
[58] Field of Search ............... 530/317; 514/11

[56] References Cited

U.S. PATENT DOCUMENTS

| | | |
|---|---|---|
| 4,517,686 | 5/1985 | Ruoslahti et al. |
| 4,578,079 | 3/1986 | Ruoslahti et al. |
| 4,589,881 | 5/1986 | Pierschbacher et al. |
| 4,614,517 | 9/1986 | Ruoslahti et al. |
| 4,661,111 | 4/1987 | Ruoslahti et al. |
| 4,683,291 | 7/1987 | Zimmerman et al. |
| 4,792,525 | 12/1988 | Ruoslahti et al. |
| 4,857,508 | 8/1989 | Adams et al. |
| 4,879,313 | 11/1989 | Tjoeng et al. |
| 5,041,380 | 8/1991 | Ruoslathi et al. |

FOREIGN PATENT DOCUMENTS

| | | |
|---|---|---|
| 317053 | 5/1989 | European Pat. Off. |
| 338634 | 10/1989 | European Pat. Off. |
| 341915 | 11/1989 | European Pat. Off. |
| 368486 | 5/1990 | European Pat. Off. |
| 2207922 | 2/1989 | United Kingdom |
| WO89/00200 | 1/1989 | WIPO |
| WO89/07609 | 8/1989 | WIPO |
| WO90/00178 | 1/1990 | WIPO |

OTHER PUBLICATIONS

Sixma et al., *Thrombosis Research*, 67:305-311 (1992).
Kloczewiak et al. *Biochemistry*, 23:1767-1774 (1984).
Gartner, T. K. and Bennett, J. S., *J. Biol. Chem.*, 260:11891-11894 (1985).
Kieffer, N. and Phillips, D. R., *Annu. Rev. Cell Biol.*, 36:329-357 (1990).
Plow et al., *Proc. Natl. Acad. Sci. USA*, 82: 8057-8061 (1985).

(List continued on next page.)

*Primary Examiner*—Lester L. Lee
*Assistant Examiner*—A. M. Davenport
*Attorney, Agent, or Firm*—Daryl B. Winter

[57] ABSTRACT

The invention in its broad aspects relates to peptide derivatives which are useful as inhibitors platelet function mediated by the GP IIbIIIa receptor and for the prevention of thrombus formation. The compounds of this invention are shown by the following Formula I:

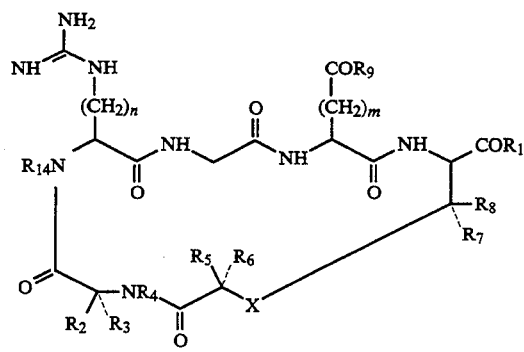

and the pharmaceutically acceptable salts thereof.

57 Claims, No Drawings

OTHER PUBLICATIONS

Pytela et al., *Proc. Natl. Acad. Aci. USA*, 82: 5766–5770 (1985).
Pytela et al., *Cell*, 40: 191–198 (1985).
Pytela et al., *Science*, 231: 1559–1562 (1985).
Gardner, et al., *Cell*, 42:439–448 (1985).
Ruggeri et al., *Proc. Natl. Acad. Sci.*, 83: 5708–5712 (1986).
Spatola, A. F. and Krzysztof, D., *Tetrahedron*, 44(3): 821–833 (1988).
Gero, T. and spatola, A. F., *Biochem Biophys, Res. Comm.*, 120(3): 840–845 (1984).
Edwards, J. V. and Spatola, A. F., *Biochem Biophys. Res. Comm.*, 136(2: 730–736 (1986).
Spatola, A. F. and Edwards, J. V. *Biopolymers*, 25: S229–S244 (1986).
Ginsberg et al., *J. Biol. Chem.*, 260: 3931–3936 (1985).
Pierschbacher et al., *Proc. Natl. Acad. Sci.*, 81:5985–5988 (1984).
Pierschbacher et al., *Nature*, 309:30–33 (1984).
D'Souza et al., *J. Biol. Chem.*, 26: 33943–3951 (1988).
Parise et al., *J. Biol. Chem.*, 262: 12597–12602 (1987).
Toda et al., *J. Cell. Biol.*, 105: 3097–3104 (1987).
Singer et al., *J. Cell. Biol.*, 104: 573–584 (1987).
Lash et al., *Develop Biol.*, 123: 411–420 (1987).
Haskel et al., *Thromb, Res.*, 56: 687–695 (1989).
Ali et al., *Peptides Proc. 11th Amer. Peptide Symposium*, La Jolla, CA, Marshall & Rivier, eds. (Jul. 9–14, 1989).
Pierschbacher et al., *J. Biol. Chem.*, 262: 17294–298 (1987).
Garsky et al., *Pro. Natl. Acad. Sci. USA*, 86: 4022–4026 (1989).
Dennis et al., *Pro Natl. Acad. Sci. USA*, 87: 2471–2475 (1989).
Chao et al., *Pro. Natl. Acad. Sci. USA*, 86: 8050–8054 (1989).
Shebuski et al., *J. Biol. Chem.*, 264: 21550–21556(1989).
Gan et al., *J. Biol. Chem.*, 263: 19827–19832 (1989).
Huang et al., *Biochemistry*, 28: 661–666 (1989).
Huang et al., *J. Biol. Chem.*, 262: 16157–1613 (1987).
Joubert, Francois J. & Taljaard, Nico, *Biochimica et Biophysica Acta*, 579: 228–233 (1979).
Pierschbacher et al., J. Biol. Chem., vol. 282, No. 86, 1987, pp. 17294–17298.

CYCLIZED PEPTIDES AND THEIR USE AS PLATELET AGGREGATION INHIBITORS

FIELD OF THE INVENTION

The present invention is directed to inhibitors of platelet aggregation which prevent binding of ligands to the glycoprotein IIbIIIa receptor (GP IIbIIIa) and therapeutic applications of the inhibitors in diseases for which blocking of platelet aggregation and intracellular adhesion mediated by (GP IIbIIIa) is indicated. The present invention is specifically directed to inhibitors which, by blocking the the binding of fibrinogen (and/or related ligands such as fibronectin, vitronectin and von Willebrands factor) to the platelet GP IIbIIIa receptor, antagonize the final common pathway of platelet aggregation and act as potent antithrombotics.

BACKGROUND OF THE INVENTION

Platelets are particles found in whole blood which participate in the process of thrombus formation and blood coagulation. A membrane bound glycoprotein, commonly known as GP IIbIIIa, is present on the exterior surface of platelets. Glycoprotein IIbIIIa is a non-covalent, calcium ion dependent heterodimer complex comprised of alpha and beta subunits (Jennings, et al., J. Biol. Chem. (1982) 257, 10458) and contributes to normal platelet function through interactions with Arg-Gly-Asp containing proteins such as fibrinogen. The interaction of GP IIbIIIa with fibrinogen is stimulated by certain factors released or exposed when a blood vessel is injured. Multiple factors, including a variety of physiologic stimuli and soluble mediators, initiate platelet activation via several pathways. These pathways have a common final step which is the activation of the GP IIbIIIa receptor on the platelet surface and its subsequent binding to fibrinogen followed by aggregation and thrombus formation. By virtue of these interactions GP IIbIIIa is a component of the platelet aggregation system (Pytela et al., Science (1986) 231, 1559). Thus, inhibition of the interaction of GP IIbIIIa with Arg-Gly-Asp containing ligands such as fibrinogen is a useful means of modulating thrombus formation. An inhibitor which prevents this binding interaction would antagonize platelet activation by any stimulus and therefore would have important antithrombotic properties.

Many common human disorders are characteristically associated with a hyperthrombotic state leading to intravascular thrombi and emboli. These are a major cause of medical morbidity, leading to infarction, stroke and phlebitis and of mortality from stroke and pulmonary and cardiac emboli. Patients with atherosclerosis are predisposed to arterial thromboembolic phenomena for a variety of reasons. Atherosclerotic plaques form niduses for platelet plugs and thrombii that lead to vascular narrowing and occlusion, resulting in myocardial and cerebral ischemic disease. This may happen spontaneously or following procedures such as angioplasty or endarteroectomy. Thrombii that break off and are released into the circulation cause infarction of different organs, especially the brain, extremities, heart and kidneys.

In addition to being involved in arterial thrombosis platelets may also play a role in venous thrombosis. A large percentage of such patients have no antecedent risk factors and develop venous thrombophlebitis and subsequent pulmonary emboli without a known cause. Other patients who form venous thrombi have underlying diseases known to predispose to these syndromes. Some of these patients may have genetic or aquired deficiencies of factors that normally prevent hypercoagulability, such as antithrombin-3. Others have mechanical obstructions to venous flow, such as tumor masses, that lead to low flow states and thrombosis. Patients with malignancy have a high incidence of thrombotic phenomena for unclear reasons. Antithrombotic therapy in this situation with currently available agents is dangerous and often ineffective.

Patients whose blood flows over artificial surfaces, such as prosthetic synthetic cardiac valves or through extracorporeal perfusion devices, are also at risk for the development of platelet plugs, thrombii and emboli. It is standard practice that patients with artficial cardiac valves be chronically anti-coagulated. However, in all instances, platelet activation and emboli formation may still occur despite adequate anticoagulation treatment.

Thus a large category of patients, including those with atherosclerosis, coronary artery disease, artificial heart valves, cancer, and a history of stroke, phlebitis, or pulmonary emboli, are candidates for limited or chronic antithrombotic therapy. The number of available therapeutic agents is limited and these, for the most part, act by inhibiting or reducing levels of circulating clotting factors. These agents are frequently not effective against the patient's underlying hematologic problem, which often concerns an increased propensity for platelet aggregation and adhesion. They also cause the patient to be susceptible to abnormal bleeding. Available antiplatelet agents, such as aspirin, inhibit only part of the platelet activation process and are therefore often inadequate for therapy.

An agent which effectively inhibits the final common pathway of platelet activation, namely fibrinogen binding to the GP IIbIIIa receptor, should accordingly be useful in a large group of disorders characterized by a hyperthrombotic state as described above. The present invention contemplates such an agent which is a new composition, namely a cyclic polypeptide consisting in part of natural amino acids and in part of unnatural amino acids. This new composition interferes with the interaction of Arg-Gly-Asp containing peptides, particularly fibrinogen, with the GP IIbIIIa complex thereby preventing platelet aggregation. Platelet aggregation has been identified as an early step in the formation of platelet plugs, emboli and thrombii in the circulatory system which in turn have been shown to play an active role in cardiovascular complications and disease. Inhibition of fibrinogen binding to the GP IIbIIIa complex has been shown to be an effective antithrombotic treatment in animals (H. K. Gold, et al., Circulation (1988) 77, 670–677; T. Yasuda, et al., J. Clin. Invest. (1988) 81, 1284–1291; B. S. Coller, et al., Blood (1986) 68, 783–786.)

Other proteins such as fibronectin contain the Arg-Gly-Asp sequence of amino acids. Large polypeptide fragments of fibronectin have been shown to have activity for cell attachment to various surfaces which has been disclosed in U.S. Pat. Nos. 4,517,686; 4,589,881; and 4,661,111. These large polypeptides contain the amino acid sequence Arg-Gly-Asp-Ser in the interior portion of the polypeptide chain. Short peptides derived from the large polypeptides were also found to promote cell attachment to various substrates when bound on the substrate. Alternatively, the same short peptides were found to inhibit cell attachment to the same substrates when dissolved or suspended in the medium surrounding the substrate. This activity has been disclosed in U.S. Pat. Nos. 4,578,079 and 4,614,517. The short peptides were defined as Q-Arg-Gly-Asp-AA1-B wherein Q is hydrogen or an amino acid; AA1 is serine, threonine, or cysteine; and B is hydroxy or an amino acid.

A number of synthetic peptides have been disclosed as inhibitors of fibrinogen binding to platelets all of which contain the Arg-Gly-Asp sequence. See U.S. Pat. No. 4,683,291; EP 0 319 506 A2; Plow et al., Proc. Natl. Acad. Sci. USA (1985) 8 2, 8057–8061; Ruggeri et al., Proc. Natl. Acad. Sci. USA (1986) 83, 5708–5712; Haverstick et al., Blood (1985) 66, 946–952; Plow et al., Blood (1987) 70, 110–115; and references cited in the above publications.

SUMMARY OF THE INVENTION

The invention in its broad aspects relates to peptide derivatives which are useful as inhibitors platelet function mediated by the GP IIbIIIa receptor and for the prevention of thrombus formation. The compounds of this invention are shown by the following Formula I:

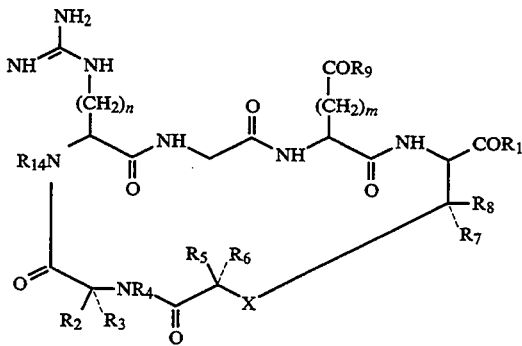

$R_1$ and $R_9$ are the same or different and are hydroxy, $C_1$–$C_8$ alkoxy, $C_2$–$C_{12}$ alkenoxy, $C_6$–$C_{12}$ aryloxy, di-$C_1$–$C_8$ alkylamino-$C_1$–$C_8$-alkoxy, acylamino-$C_1$–$C_8$-alkoxy selected from the group: acetylaminoethoxy, nicotinoylaminoethoxy, and succinamidoethoxy; pivaloyloxyethoxy, $C_6$–$C_{12}$aryl-$C_1$–$C_8$-alkoxy, hydroxy-$C_2$–$C_8$-alkoxy, dihydroxy-$C_3$–$C_8$-alkoxy, or a substituted heteroatom $NR_{10}R_{11}$;

$R_{10}$, $R_{11}$ and $R_{14}$ are the same or different and are hydrogen, $C_1$–$C_8$-alkyl, $C_3$–$C_8$-alkenyl, $C_6$–$C_{12}$-aryl, $C_6$–$C_{12}$-aryl-$C_1$–$C_8$-alkyl;

$R_2$, $R_3$, $R_5$, $R_6$, $R_7$, $R_8$ are the same or different and are hydrogen, $C_1$–$C_{12}$ alkyl which include branched and unsaturated alkyl groups; substituted $C_1$–$C_8$ alkyl where the substituent(s) can be halo, $C_1$–$C_8$ alkoxy, $C_6$–$C_{12}$ aryloxy, isothioureido, ureido, amino, $C_1$–$C_8$ alkylamino, di-$C_1$–$C_8$alkylamino, hydroxy, amino-$C_2$–$C_8$alkylthio, amino-$C_2$–$C_8$ alkoxy, acetamido, benzamido, $C_6$–$C_{12}$ arylamino, guanidino, phthalimido, mercapto, $C_1$–$C_8$ alkylthio, $C_6$–$C_{12}$ arylthio, carboxy, carboxamide, carbo-$C_1$–$C_8$alkoxy, $C_6$–$C_{12}$ aryl-$C_1$–$C_8$alkyl, $C_6$–$C_{12}$ aryl-$C_2$–$C_8$ alkenyl, aromatic heterocyclo-$C_1$–$C_8$ alkyl or aromatic heterocyclo-$C_2$–$C_8$ alkenyl wherein the heterocyclic groups have 5–10 ring atoms and contain up to two O, N, or S heteroatoms; substituted $C_6$–$C_{12}$-aryl-$C_1$–$C_8$alkyl or substituted aromatic heterocyclo-$C_1$–$C_8$ alkyl wherein the substituent(s) is halo, dihalo, $C_1$–$C_8$ alkyl, hydroxy, $C_1$–$C_8$ alkoxy, amino, guanidino, isothioureido, ureido, amino $C_1$–$C_8$alkyl, phenyloxy, acetamido, benzamido, di-$C_1$–$C_8$alkylamino, $C_1$–$C_8$ alkylamino, carboxyl, $C_6$–$C_{12}$ aroyl, $C_1$–$C_8$ alkanoyl and the heterocyclic groups are as defined above.

$R_4$ is hydrogen, $C_1$–$C_8$ alkyl, $C_3$–$C_{10}$ cycloalkyl, $C_6$–$C_{12}$ aryl, or $C_6$–$C_{12}$ aryl-$C_1$–$C_8$-alkyl;

$R_2$ and $R_3$, $R_5$ and $R_6$, or $R_7$ and $R_8$ may be joined together to form a ring of three to six carbon atoms or a ring of two to five carbon atoms and one O or S heteroatom or substituted heteroatom $NR_{12}$;

$R_{12}$ is $C_1$–$C_8$-alkyl, $C_3$–$C_8$-alkenyl, $C_6$–$C_{12}$-aryl, $C_6$–$C_{12}$-aryl-$C_1$–$C_8$-alkyl, $C_1$–$C_8$ alkanoyl, or $C_6$–$C_{12}$ aroyl;

$R_2$ or $R_3$ may be joined with $R_4$ to form an alkylene bridge of from two to five carbon atoms or an alkylene bridge of from two to four carbon atoms and one O or S heteroatom;

X is an O or S heteroatom or S heteroatom bearing one or two O heteroatoms or substituted $NR_{13}$ heteroatom or a methylene group;

$R_{13}$ is hydrogen, $C_1$–$C_8$-alkyl, $C_3$–$C_8$-alkenyl, $C_6$–$C_{12}$-aryl, $C_6$–$C_{12}$-aryl-$C_1$–$C_8$-alkyl, $C_1$–$C_8$ alkanoyl, or $C_6$–$C_{12}$ aroyl;

n is an integer from 1 to 6;

m is an integer from 0 to 4;

and the pharmaceutically acceptable salts thereof.

As used throughout this document, including the claims, and unless specified otherwise: alkyl, alkenyl and alkynyl denote straight and branched hydrocarbon chains having single, double and triple bonds, respectively; $C_6$–$C_{12}$ aryl groups denote unsubstituted aromatic ring or fused rings such as, for example, phenyl or naphthyl; hetero denotes the heteroatoms O, N, or S; aromatic heterocyclic groups have 5–10 ring atoms and contain up to four heteroatoms; halogen or halo denote F, Cl Br, or I atoms; alkoxy denotes an alkyl group attached to O.

Examples of $C_1$–$C_8$ alkyl or $C_2$–$C_8$ alkenyl groups include methyl, ethyl, propyl, isopropyl, butyl, t-butyl, pentyl, isopentyl, hexyl, vinyl, allyl, butenyl and the like; aromatic heterocyclic groups include but are not limited to, for example, pyridyl, thienyl, furyl, indolyl, benzthienyl, imidazolyl, thiazolyl, quinolinyl and isoquinolinyl.

Preferred are those compounds of the above Formula wherein:

$R_1$ and $R_9$ are the same or different and are hydroxy, $C_1$–$C_8$ alkoxy or $C_6$–$C_{12}$ aryl-$C_1$–$C_8$ alkoxy;

$R_2$, $R_3$, $R_5$, $R_6$, $R_7$, $R_8$ are the same or different and are hydrogen, $C_1$–$C_6$ alkyl which include branched and unsaturated alkyl groups; substituted $C_1$–$C_6$ alkyl where the substituent(s) can be isothioureido, ureido, amino, $C_1$–$C_4$ alkylamino, di-$C_1$–$C_4$ alkylamino, hydroxy, acetamido, benzamido, $C_6$–$C_{12}$ arylamino, guanidino, mercapto, $C_1$–$C_8$alkylthio, carboxy, carboxamide, carbo-$C_1$–$C_4$ alkoxy, $C_6$–$C_{12}$aryl-$C_1$–$C_8$ alkyl, or aromatic heterocyclo-$C_1$–$C_8$ alkyl wherein the heterocyclic groups have 5–10 ring atoms and contain up to two O, N, or S heteroatoms; substituted $C_6$–$C_{12}$ aryl-$C_1$–$C_8$ alkyl or substituted aromatic heterocyclo-$C_1$–$C_8$ alkyl wherein the substituent(s) is halo, dihalo, $C_1$–$C_4$ alkyl, hydroxy, $C_1$–$C_4$ alkoxy, amino, guanidino, isothioureido, ureido, amino-$C_1$–$C_4$ alkyl, acetamido, benzamido, di-$C_1$–$C_4$ alkylamino, $C_1$–$C_4$ alkylamino, carboxyl, $C_6$–$C_{12}$ aroyl, $C_1$–$C_4$ alkanoyl and the heterocyclic groups are as defined above.

$R_4$ is hydrogen or may be joined with $R_2$ or $R_3$ to form an alkylene bridge of from two to five carbon atoms or an alkylene bridge of from two to four carbon atoms and one O or S heteroatom;

$R_2$ and $R_3$, $R_5$ and $R_6$, or $R_7$ and $R_8$ may be joined together to form a ring of three to six carbon atoms or a ring of two to five carbon atoms and one O or S heteroatom or substituted heteroatom $NR_{12}$;

$R_{12}$ is $C_1$–$C_4$ alkyl, $C_6$–$C_{12}$-aryl, $C_6$–$C_{12}$-aryl-$C_1$–$C_4$-alkyl, $C_1$–$C_4$ alkanoyl, or $C_6$–$C_{12}$ aroyl;

X is an O or S heteroatom or S heteroatom bearing one or two O heteroatoms or substituted $NR_{13}$ heteroatom or a methylene group;

$R_{13}$ is hydrogen, $C_1$–$C_4$-alkyl, $C_6$–$C_{12}$-aryl, $C_6$–$C_{12}$-aryl-$C_1$–$C_4$alkyl, $C_1$–$C_4$ alkanoyl, or $C_6$–$C_{12}$ aroyl;

$R_{14}$ is hydrogen, $C_1$–$C_4$-alkyl, $C_6$–$C_{12}$-aryl, $C_6$–$C_{12}$-aryl-$C_1$–$C_4$-alkyl;

n is an integer from 1 to 6;

m is an integer from 0 to 4;

and the pharmaceutically acceptable salts thereof.

More preferred are compounds of the above Formula wherein:

$R_1$ and $R_9$ are the same or different and are hydroxy, $C_1$–$C_4$ alkoxy or $C_6$–$C_{12}$ aryl-$C_1$–$C_4$ alkoxy;

$R_2$, $R_3$, $R_5$, $R_6$, $R_7$, $R_8$ are the same or different and are hydrogen, $C_1$–$C_6$ alkyl which include branched and unsaturated alkyl groups; substituted $C_1$–$C_6$ alkyl where the substituent(s) can be amino, $C_1$–$C_4$ alkylamino, di-$C_1$–$C_4$ alkylamino, hydroxy, acetamido, benzamido, $C_6$–$C_{12}$ arylamino, guanidino, mercapto, $C_1$–$C_8$ alkylthio, carboxy, carboxamide, carbo-$C_1$–$C_4$ alkoxy, $C_6$–$C_{12}$-aryl-$C_1$–$C_4$ alkyl, or aromatic heterocyclo-$C_1$–$C_4$ alkyl wherein the heterocyclic groups have 5–10 ring atoms and contain up to two O, N, or S heteroatoms; substituted $C_6$–$C_{12}$ aryl-$C_1$–$C_4$ alkyl or substituted aromatic heterocyclo-$C_1$–$C_4$ alkyl wherein the substituent(s) is halo, $C_1$–$C_4$ alkyl, hydroxy, $C_1$–$C_4$ alkoxy, amino, guanidino, amino-$C_1$–$C_4$ alkyl, acetamido, benzamido, di-$C_1$–$C_4$ alkylamino, $C_1$–$C_4$ alkylamino, carboxyl, $C_6$–$C_{12}$ aroyl, $C_1$–$C_4$ alkanoyl and the heterocyclic groups are as defined above.

$R_4$ is hydrogen or may be joined with $R_2$ or $R_3$ to form an alkylene bridge of from two to five carbon atoms or an alkylene bridge of from two to four carbon atoms and one O or S heteroatom;

$R_2$ and $R_3$, $R_5$ and $R_6$, or $R_7$ and $R_8$ may be joined together to form a ring of three to six carbon atoms or a ring of two to five carbon atoms and one O or S heteroatom or substituted heteroatom $NR_{12}$;

$R_{12}$ is $C_1$–$C_4$ alkyl, $C_6$–$C_{12}$-aryl, $C_6$–$C_{12}$-aryl-$C_1$–$C_4$-alkyl, $C_1$–$C_4$ alkanoyl, or $C_6$–$C_{12}$ aroyl;

X is an O or S heteroatom or S heteroatom bearing one or two O heteroatoms or substituted $NR_{13}$ heteroatom or a methylene group;

$R_{13}$ is hydrogen, $C_1$–$C_4$ alkyl, $C_6$–$C_{12}$-aryl, $C_6$–$C_{12}$-aryl-$C_1$–$C_4$alkyl, $C_1$–$C_4$ alkanoyl, or $C_6$–$C_{12}$ aroyl;

$R_{14}$ is hydrogen, $C_1$–$C_4$-alkyl, $C_6$–$C_{12}$-aryl, $C_6$–$C_{12}$-aryl-$C_1$–$C_4$-alkyl;

n is an integer from 2 to 4;

m is an integer from 1 to 3;

and the pharmaceutically acceptable salts thereof.

Most preferred are compounds of the above Formula wherein:

$R_1$ and $R_9$ are the same or different and are hydroxy, $C_1$–$C_4$ -alkoxy or benzyloxy;

$R_2$ or $R_3$ is hydrogen and the remaining substituent is hydrogen, $C_1$–$C_6$ alkyl which includes branched alkyl groups or substituted $C_1$–$C_6$ alkyl where the substituent can be amino, hydroxy, mercapto, carboxy, carboxamide, guanidino, phenyl or hydroxyphenyl, indolyl, or imidazolyl;

$R_5$ or $R_6$ is hydrogen and the remaining substituent is hydrogen, phenyl $C_1$–$C_6$ alkyl which includes branched alkyl groups or substituted $C_1$–$C_6$ alkyl where the substituent can be amino, hydroxy, mercapto, carboxy, carboxamide, guanidino, phenyl or hydroxyphenyl, indolyl, or imidazolyl;

$R_7$ or $R_8$ is hydrogen or $C_1$–$C_6$ alkyl which includes branched alkyl groups and the remaining substituent is hydrogen, $C_1$–$C_6$ alkyl which includes branched alkyl groups or substituted $C_1$–$C_6$ alkyl where the substituent can be amino, hydroxy, mercapto, carboxy, carboxamide, guanidino, phenyl or hydroxyphenyl, indolyl, or imidazolyl;

$R_4$ is hydrogen or may be joined with $R_2$ or $R_3$ to form an alkylene bridge of three or four carbon atoms or an alkylene bridge of two carbon atoms and one S heteroatom;

X is an O or S heteroatom or an S heteroatom bearing one or two O heteroatoms;

$R_{14}$ is hydrogen, $C_1$–$C_4$-alkyl, $C_6$–$C_{12}$-aryl, $C_6$–$C_{12}$-aryl-$C_1$–$C_4$-alkyl;

n is 3;

m is 1;

and the pharmaceutically acceptable salts thereof.

The present invention includes a method for reducing platelet aggregation in a mammal. This method involves administering a therapeutically effective amount of the compounds of the present invention alone or in combination with a pharmacologically acceptable carrier. This general method may also be applied to treat a mammal who has an increased propensity for thrombus formation.

Additionally, the present invention is directed to compositions of matter for reducing platelet aggregation in a mammal; treating a mammal who has an increased propensity for thrombus formation; or inhibiting binding of a ligand to GP llbllla in a mammal; wherein each of these compositions contains as an active ingredient one or more of the cyclic peptides defined in Formula I.

DETAILED DESCRIPTION OF THE INVENTION

The products of Formula I and the preferred substituents can be made by using one of the methods depicted below. The definitions of the substituent groups are the same as for Formula I except where noted.

Method A

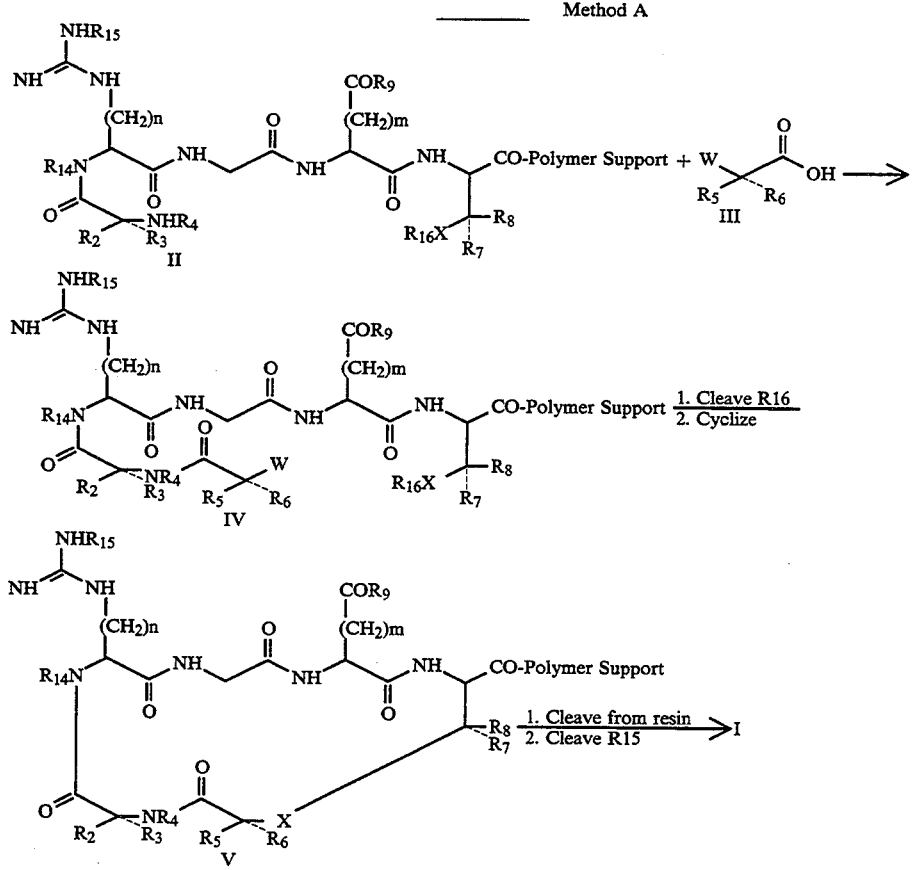

A peptide derivative bound to a polymer support, depicted by intermediate II, may be prepared by sequential coupling of individual amino acid derivatives by standard techniques. (Merrifield, R. B., J. Am. Chem. Soc. (1963)85, 2149–2154; Stewart, J. M. and Young, J. D., Solid Phase Peptide Synthesis (1984), Pierce Chemical Co., Rockford, Ill. and additonal references cited in the above publications). When the tetrapeptide derivative II is obtained, the terminal amino group is acylated with a suitable carboxylic acid derivative III. The acylation to yield IV may be accomplished using a number of standard methods which require activation of the carboxylic acid group of III. For example, activation may be obtained by the addition of an equimolar amount of dicyclohexylcarbodiimide or related carbodiimide reagent. If desired an additive such as 1-hydroxybenztriazole or N-hydroxysuccinimide may be incorporated. Alternatively, the carboxyl group may be activated by conversion to a halo derivative. For example, the chloride may be obtained by treatment of the acid with thionyl chloride or oxalyl chloride in a compatible solvent such as dichloromethane, toluene, or ethylene dichloride if desired. The substituent W is chosen such that it is readily displaceable by the group X. Suitable substituents W are, for example, halo atoms such as bromine or iodine or activated oxygen functions such as methanesulfonyloxy or p-toluensulfonyloxy and related sulfonic acid esters.

Cyclization to the resin bound intermediate V may be accomplished by selectively exposing the nucleophilic group X by removal of $R_{16}$ and allowing X to react such that it displaces group W with formation of a new chemical bond. For example, if X is a sulfur or oxygen atom and $R_{16}$ is a triphenylmethyl group, then $R_{16}$ may be selectively cleaved from X using a very dilute solution of a strong acid such as trifluoroacetic acid in a solvent compatible with the polymer resin. Examples of resin compatible solvents are dimethylacetamide, dimethylformamide or dichloromethane and the like.

The end result of the cleavage process is replacement of the $R_{16}$ group with a hydrogen atom. After cleavage of $R_{16}$, the resin bound peptide derivative V ($R_{16}$=H) is allowed to react in a suitable solvent such as dimethylacetamide until cyclization is complete. If desired, a base such as N-methylmorpholine may be incorporated into the reaction. Other protecting groups in the peptide molecule IV must be stable to the reaction conditions chosen to form V. For example, $R_9$ may be a group which affords an ester such as methoxy, ethoxy, benzyloxy, t-butyloxy and the like or an amide or substituted amide. $R_{15}$ may be an arylsulfonyl group such as 2,2,5,7,8-pentamethylchroman-6-sulfonyl (PMC) or p-methoxybenzenesulfonyl. Final cleavage of the cyclized peptide product from the polymer resin may be accomplished in a variety of ways dependent upon the type of resin used and the chemical linkage between the cyclized peptide and the resin. If, for example, the resin is derived from a polymerized p-alkoxybenzyl alcohol derivative, then cleavage of the peptide-resin linkage may be carried out using a strong acid such as trifluoroacetic acid. If desired, additives such as phenol, anisole and ethanedithiol may be added to the reaction.

The groups $R_9$ and $R_{15}$ may be chosen, if desired, to also be cleavable concurrently with cleavage of the cyclized peptide from the polymer resin. Examples of such chemical groups are $R_9$=t-butyloxy, cleavage of which yields $R_9$=OH and $R_{15}$=2,2,5,7,8-pentamethylchroman-6-sulfonyl, cleavage of which affords $R_{15}$=H. The crude product thus obtained may be further purified using chromatographic or other methods of chemical purification to obtain I.

Further derivatization of I may be carried out if so desired. For example, if X=S, treatment of I with a stoichiometric amount of an oxidizing agent such as 3-chloroperoxybenzoic acid or similar agent will produce the sulfoxide derivative where X=SO. Use of an excess amount of oxidant will afford the sulfone derivative where X=SO$_2$.

Georg Thieme Verlag, Stuttgart 1974). The attached substituents $R_1$, $R_9$, $R_{15}$ and $R_{16}$ may be chosen such that they are transformable concurrently or sequentially as described in Methods A and B above. Cyclization of VI wherein $R_{16}$=H under conditions described above in Method B will provide compounds of Formula I.

The starting materials required for the processes described herein are known in the literature or can be prepared using known methods and known starting materials.

ISOMER PRODUCTS

In products of Formula I carbon atoms bonded to

Method B

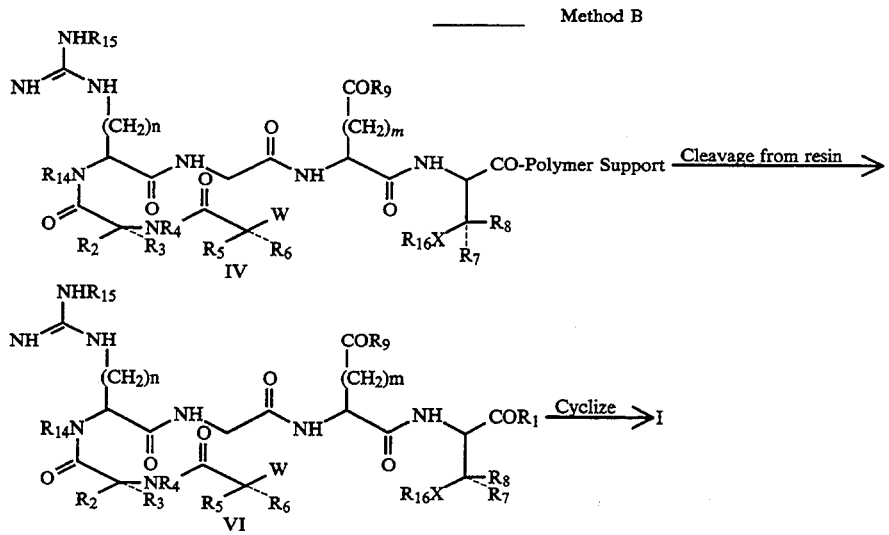

Alternatively, the linear peptide derivative IV, prepared as described above in Method A, may be cleaved from the resin prior to cyclization to yield VI. For example, if IV is synthesized on a polystyrene resin the cleavage can be accomplished using liquid hydrogen flouride. The groups $R_9$, $R_{15}$ and $R_{16}$ may, if desired, be cleaved concurrently under these conditions. If concurrent cleavage is desired, then examples of suitable substituents are $R_9$=t-butyloxy or cyclohexyloxy, $R_{15}$=p-toluenesulfonyl or 2,2,5,7,8-pentamethylchroman-6-sulfonyl and $R_{16}$=triphenylmethyl if X=O, S or t-butoxycarbonyl if X=NR$_{13}$. Cleavage of these groups would result in $R_9$=OH and $R_{15}$ and $R_{16}$=H. The peptide derivative VI may then be cyclized in solution in the presence of a weak base such as ammonium hydroxide. The group W is as described in Method A. The resulting crude I may then be purified as described above in Method A.

The purified I may be futher transformed as described in Method A. Additionally and if desired, when X=NR$_{13}$ and $R_{13}$=H, I may be acylated with, for example, acetyl chloride, acetic anhydride or benzoyl chloride, methanesulfonyl chloride or p-toluenesulfonyl chloride and the like.

Method C

Intermediate VI may be prepared by the sequential coupling of amino acid derivatives in solution without the use of polymer resin or other solid supports. The methods useful for solution phase peptide synthesis are well documented in the chemical literature and are known to those skilled in the art. (Houben-Weyl, Methoden der Organischen Chemie, 4th Edn., Vol. 15, four nonidentical substituents are asymmetric. Accordingly, the compounds may exist as diastereoisomers, enantiomers or mixtures thereof. The syntheses described above may employ racemates, enantiomers or diastereomers as starting materials or intermediates. Diastereomeric products resulting from such syntheses may be separated by chromatographic or crystallization methods. Likewise, enantiomeric product mixtures may be separated using the same techniques or by other methods known in the art. Each of the asymmetric carbon atoms, when present in compounds of Formula I, may be in one of two configurations (R or S) and both are within the scope of the present invention. The carbon atoms bearing the (CH$_2$)$_n$ sidechain and the (CH$_2$)$_m$ sidechain are generally preferred to have the S configuration. The carbon atom bearing the substituents $R_2$ and $R_3$ is generally preferred to have a configuration corresponding to that of a D amino acid. The configuration may be assigned R or S depending on the chemical composition of $R_2$ and $R_3$.

The compounds described in this invention may be isolated as or converted to salts of various inorganic and organic acids and bases. Such salts are within the scope of this invention. Examples of such salts include ammonium, metal salts like sodium, potassium, calcium and magnesium; salts with organic bases like dicyclohexylamine, N-methyl-D-glucamine and the like; and salts with amino acids like arginine or lysine. Salts with inorganic and organic acids may be likewise prepared, for example, using hydrochloric, hydrobromic, sulfuric, phosphoric, trifluoroacetic. methanesulfonic, malic, maleic, fumaric and the like. Non-toxic and physiologically compatible salts are particularly useful although other less desireable salts may have use in the processes of isolation and purification.

A number of methods are useful for the preparation of the salts described above and are known to those skilled in the art. For example, reaction of the free acid or free base form of a compound of Formula I with one or more molar equivalents of the desired acid or base in a solvent or solvent mixture in which the salt is insoluble; or in a solvent like water after which the solvent is removed by evaporation, distillation or freeze drying. Alternatively, the free acid or base form of the product may be passed over an ion exchange resin to form the desired salt or one salt form of the product may be converted to another using the same general process.

The compounds described in the present invention inhibit the binding of fibrinogen to its receptor on platelets, GP llblla, and thus prevent the aggregation of platelets and the formation of platelet plugs, emboli and thrombii in the circulatory system in mammals. Thromboembolic disorders have been shown to be directly related to the susceptibility of blood platelets to aggregate. Mammals exposed to medical procedures such as angioplasty and thrombolytic therapy are particularly susceptible to thrombus formation. The compounds of the present invention can be used to inhibit thrombus formation following angioplasty. They may also be used in combination with thrombolytic agents such as tissue plasminogen activator and its derivatives (U.S. Pat. Nos. 4,752,603; 4,766,075; 4,777,043; EP 199,574; EP 0238,304; EP 228,862; EP 297,860; PCT WO89/04368; PCT WO89/00197), streptokinase and its derivatives, or urokinase and its derivatives to prevent arterial reocclusion following thrombolytic therapy. When used in combination with the above thrombolytic agents, the compounds of the present invention may be administered prior to, simultaneously with, or subsequent to the antithrombolytic agent. Mammals exposed to renal dialysis, blood oxygenation, cardiac catheterization and similar medical procedures as well as mammals fitted with certain prosthetic devices are also susceptible to thromboembolic disorders. Physiologic conditions, with or without known cause may also lead to thromboembolic disorders. Thus, the compounds described herein are useful in treating thromboembolic disorders in mammals. The compounds described herein may also be used as adjuncts to anticoagulant therapy, for example in combination with aspirin, heparin or warfarin and other anticoagulant agents. The application of the compounds described herein for these and related disorders will be apparent to those skilled in the art.

PLATELET INHIBITION ASSAYS

The evaluation of inhibitors of the fibrinogen—platelet interaction is guided by in vitro receptor binding assays and in vitro platelet aggregation inhibition assays.

In-vitro biological activity of the compounds of Formula I was monitored using a modified fibrinogen—GP llblla ELISA based on the method of Nachman and Leung (J. Clin. Invest. (1982) 69, 263-269) which measures the inhibition of fibrinogen binding to purified human platelet GP llblla receptor. Human fibrinogen was prepared by the method of Lipinska, et al. (J. Lab. Grin. Med. (1974) 84, 509-516). Platelet GP llblla was prepared by the method of Fitzgerald, et al. (Anal. Blochem. (1985) 151,169-177.

Microtiter plates are coated with fibrinogen (10 ug/ml) and then blocked with TACTS buffer containing 0.5% bovine serum albumin (BSA). (TACTS buffer contains 20 mM Tris. HCl, pH 7.5, 0.02% sodium azide, 2 mM calcium chloride, 0.05% Tween 20, 150 mM sodium chloride.) The plate is washed with phosphate buffered saline (PBS) containing 0.01% Tween 20 and the sample to be determined added, followed by addition of solubilized GP llblla receptor (40 ug/ml) in TACTS, 0.5% BSA. After incubation, the plate is washed and 1 ug/ml of murine anti-platelet monoclonal antibody AP3 (P. J. Newman et al. Blood (1985) 65, 227-232) is added. After another wash a goat anti-mouse IgG conjugated to horseradish peroxidase is added. A final wash is performed and developing reagent buffer (10 mg o-phenylenediamine dihydrochloride, 0.0212% hydrogen peroxide, 0.22 mM citrate, 50 mM phosphate, pH 5.0) is added and then incubated until color develops. The reaction is stopped with 1N sulfuric acid and the absorbance at 492 nm is recorded.

In addition to the GP llblla ELISA assay, platelet aggregation assays may be performed in human platelet rich plasma (PRP). Fifty milliliters of whole human blood (9 parts) is drawn on 3.6% sodium citrate (1 part) from a donor who has not taken aspirin or related medications for at least two weeks. The blood is centrifuged at 160 ×g for 10 min at 220° C. and then allowed to stand for 5 min after which the PRP is decanted. Platelet poor plasma (PPP) is isolated from the remaining blood after centrifugation at 2000×g for 25 min. The platelet count of the PRP was diluted to ca. 300000 per microliter with PPP.

A 225 uL aliquot of PRP plus 25 uL of either a dilution of the test sample or a control (PBS) is incubated for 5 min in a Chrono-log Whole Blood Aggregometer at 25° C. An aggregatng agent (collagen, 1 ug/ml; U46619, 100 ng/ml; or ADP, 8 uM) is added and the platelet aggregation recorded.

In the management of thromboembolic disorders the compounds of this invention may be utilized in compositions such as tablets, capsules or elixers for oral administration; suppositories for rectal administration; sterile solutions or suspensions for injectable administration, and the like. Animals in need of treatment using compounds of this invention can be administered dosages that will provide optimal efficacy. The dose and method of adminstration will vary from animal to animal and be dependent upon such factors as weight, diet, concurrent medication and other factors which those skilled in the medical arts will recognize.

DOSAGE FORMULATIONS

Dosage formulatons of the cyclic polypeptides of the present invention are prepared for storage or administration by mixing the the cyclic polypeptide having the desired degree of purity with physiologically acceptable carriers, excipients, or stabilizers. Such materials are non-toxic to the recipients at the dosages and concentrations employed, and include buffers such as phosphate, citrate, acetate and other organic acid salts; antioxidants such as ascorbic acid; low molecular weight (less than about ten residues peptides such as polyarginine, proteins, such as serum albumin. gelatin, or immunoglobulins; hydrophilic polymers such as polyvinylpyrrolidinone; amino acids such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sobitol; counterions such as sodium and/or nonionic surfactants such as Tween, Pluronics or polyethyleneglycol.

Dosage formulations of the cyclic polypeptides of the present invention to be used for therapeutic administration must be sterile. Sterility is readily accomplished by filtration through sterile filtration membranes such as 0.2 micron membranes. Cyclic polypeptide formulations ordinarily will be stored in lyophilized form or as an aqueous solution. The pH of the cyclic polypeptide preparations typically will be between 3 and 11, more preferably from 5 to 9 and most preferably from 7 and 8. It will be understood that use of certain of the foregoing excipients, carriers, or stabilizers will result in the formation of cyclic polypeptide salts. While the preferred route of administration is by hypodermic injection needle, other methods of administration are also anticipated such as suppositories, aerosols, oral dosage formulations and topical formulations such as ointments, drops and dermal patches.

Therapeutic cyclic polypeptide formulations generally are placed into a container having a sterile access port, for example, an intravenous solution bag or vial having a stopper pierceable by hypodermic injection needle.

Therapeutically effective dosages may be determined by either in vitro or in vivo methods. One method of evaluating therapeutically effective dosages is illustrated in Example 42 where the cyclic polypeptide cyclo-S-acetyl-Gly-Arg-Gly-Asp-Cys-OH was determined to have a 50% inhibitory concentration (IC$_{50}$)of 5 nM when inhibiting fibrinogen binding to the GP llbllla platelet receptor. Similarly, in a platelet aggregation assay in Example 43 using the same cyclic peptide, the IC$_{50}$ was found to be 8.5 uM. Based upon such in vitro assay techniques, a therapeutically effective dosage range may be determined. For each particular cyclic polypeptide of the present invention, individual determinations may be made to determine the optimal dosage required. The range of therapeutically effective dosages will naturally be influenced by the route of administration. For injection by hypodermic needle it may be assumed the dosage is delivered into the body's fluids. For other routes of administration, the absorption efficiency must be individually determined for each cyclic polypeptide by methods well known in pharmacology.

The range of therapeutic dosages may range from 0.001 nM to 1.0 mM, more preferably from 0.1 nM to 100 uM, and most preferably from 1.0 nM to 50 uM.

Typical formulation of compounds of Formula I as pharmaceutical compositions are discussed below.

About 0.5 to 500 mg of a compound or mixture of compounds of Formula I, as the free acid or base form or as a pharmaceutically acceptable salt, is compounded with a physiologically acceptable vehicle, carrier, excipient, binder, preservative, stabilizer, flavor, etc., as called for by accepted pharmaceutical practice. The amount of active ingredient in these compositions is such that a suitable dosage in the range indicated is obtained.

Typical adjuvants which may be incorporated into tablets, capsules and the like are a binder such as acacia, corn starch or gelatin; an excipient such as microcrystalline cellulose; a disintegrating agent like corn starch or alginic acid; a lubricant such as magnesium stearate; a sweetening agent such as sucrose or lactose; a flavoring agent such as peppermint, wintergreen or cherry. When the dosage form is a capsule, in addition to the above materials it may also contain a liquid carrier such as a fatty oil. Other materials of various types may be used as coatings or as modifiers of the physical form of the dosage unit. A syrup or elixer may contain the active compound, a sweetener such as sucrose, preservatives like propyl paraben, a coloring agent and a flavoring agent such as cherry. Sterile compositions for injection can be formulated according to conventional pharmaceutical practice. For example, dissolution or suspension of the active compound in a vehicle such as water or naturally occuring vegetable oil like sesame, peanut, or cottonseed oil or a synthetic fatty vehicle like ethyl oleate or the like may be desired. Buffers, preservatives, antioxidants and the like can be incorporated according to accepted pharmaceutical practice.

EXAMPLES

In the following Examples, amino acids may be described by the standard three letter amino acid code when refering to intermediates and final products. Standard abreviations are listed in The Merck Index, 10th Edition, pp Misc-2- Misc-3. Unless otherwise designated the amino acids have the natural or "l"-configuration at the alpha carbon atom. If the code is preceded by a "d" this signifies the unnatural amino acid enantiomer. If the product or intermediate name is preceded by "cyclo" this shall be taken to mean that the peptide has been cyclized via the heteroatom X, e.g. compounds of Formula I or V.

Example 1

Bromoacetyl-Gly-Arg-Gly-Asp-Cys-OH

The title compound is prepared in protected form by standard solid phase peptide synthesis on 2% crosslinked polystyrene resin (Merrifield resin). Treatment of the resin bound intermediate with liquid hydrogen fluoride induces concommitant cleavage of the protecting groups from the title compound as well as cleavage of the peptide from the resin. The crude peptide is purified by reverse phase high performance liquid chromatography (HPLC) using a 4.6 mm ×250 mm column containing 10 micron, 300 Angstrom pore size C-18 packing. The elution of the column is with an acetontrile/0.1% aqueous trifluoroacetic acid gradient going from 0%–40% acetonitrile linearly over 80 minutes. The title compound elutes at 14 minutes. FAB mass spectrum: calc. 627; obs. 628 (M+I).

Example 2 cyclo-S-acetyl-Gly-Arg-Gly-Asp-Cys-OH

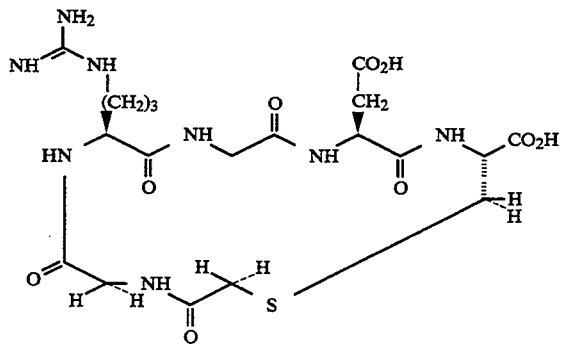

The compound prepared in Example 1 is dissolved in deionized water (1 mg/ml) and the pH of the solution is adjusted to 8.0-8.5 with ammonium hydroxide. After stirring for 4 hr at ambient temperature the reaction solution is acidified to pH 3.0-3.5 with trifluoroacetic acid and then lyophilized. The resulting crude product is purified by HPLC using the conditions described in Example 1. The desired title compound elutes after 11 minutes. FAB mass spectrum: calc. 546; obs. 547 (M+1). Amino acid analysis: carboxymethyl-cys, 0.96; Asp, 1.04; Gly, 2.12; Arg, 0.94. 1H NMR(300 mhz, $D_2O$, pH 7): 4.75, m; 4.3-4.4, m; 4.15, d; 4.0, ab q; 3.9, d; 3.4, ab q; 3.2, t; 2.95-3.15, m; 2.7, dq; 1.75-2.05, m; 1.55-1.7, m.

Example 3 cyclo-S-acetyl-Gly-Arg-Gly-Asp-Cys-OH

Bromoacetyl-Gly-Arg(g-2,2,5,7,8-pentamethylchroman-6-sulfonyl)-Gly-Asp(beta-t-butyl)-Cys(S-triphenylmethyl)-O-(polymer resin) is prepared using standard solid phase peptide synthesis utilizing fluorenylmethoxycarbonyl (FMOC) protecting group chemistry on a p-alkoxybenzyl alcohol resin. Repeated treatment of the resin bound peptide with a 1% solution of trifluoroacetic acid in dichloromethane results in cleavage of the S-triphenylmethyl group as evidenced by the bright yellow of the solution. Treatment is continued until dissipation of the yellow color (ca. 1.5 L of the cleavage solution is required per gram of resin bound peptide.) After complete cleavage of the S-triphenylmethyl group, the resin bound peptide is washed several times with a 5% solution of N-methylmorpholine in dimethylacetamide and then shaken in pure dimethylacetamide for 12 hr to complete the cyclization. Treatment of the cyclized resin bound peptide with trifluoroacetic acid containing (v/v) 1% phenol, 1% anisole and 1% ethanedithiol effects concommitant cleavage of the remaining protective groups and cleavage of the desired product from the resin. Purification of the crude product as described in Example 2 affords the title compound identical to that described above.

Using the method described in Example 3, the compounds listed in Examples 4-15 may be prepared. The compounds are depicted by Formula VII and are derivatives of Formula I wherein $R_1=R_9=OH$, $R_5=R_6=R_7=R_8=R_{14}=H$, X=S, n=3, m=1, the chirality of the asymmetric carbon atoms bearing the $(CH_2)_n$ and $(CH_2)_m$ sidechains are each S, the chirality of the asymmetric carbon atom bearing the $R_1$ substituent is R and the remaining substituents are as described in the following individual examples. Crude products are purified using HPLC as described in Example 2.

Example 4

A compound of Formula VII as described above and with $R_2=CH_2CONH_2$, $R_3=H$, $R_4=H$.

Example 5

A compound of Formula VII as described above and with $R_2=H$, $R_3-CH_2CONH_2$, $R_4=H$. FAB mass spectrum: obs. 604 (m+1). HPLC retention time: 13.8 min.

Example 6

A compound of Formula VII as described above and with $R_2=CH_3CH(OH)-$, $R_3=H$, $R_4=H$. The hydroxy bearing carbon atom has the same configuration as occurs in L-threonine. FAB mass spectrum: obs. 591 (m+1). HPLC retention time: 12 min.

Example 7

A compound of Formula VII as described above and with $R_2=H$, $R_3=CH_3CH(OH)-$, $R_4=H$. The hydroxy bearing carbon atom has the same configuration as occurs in D-threonine. FAB mass spectrum: obs. 591 (m+1). HPLC retention time: 9.5 min. Amino acid analysis: S-carboxymethylCys, 1.04; Thr, 1.04; Arg, 0.99; Gly, 1.01; Asp, 1.11.

Example 8

A compound of Formula VII as described above and with $R_2=CH_3$, $R_3=H$, $R_4=H$. FAB mass spectrum: obs. 561 (m+1). HPLC retention time: 14 min.

Example 9

A compound of Formula VII as described above and with $R_2=H$, $R_3=CH_3$, $R_4=H$. FAB mass spectrum: obs. 561 (m+1). HPLC retention time: 10.5 min. Amino acid analysis:

Example 10

A compound of Formula VII as described above and with $R_2=$p-hydroxyphenyl-$CH_2$-, $R_3=H$, $R_4=H$. FAB mass spectrum: obs. 561 (m+1). HPLC retention time: 22 min.

Example 11

A compound of Formula VII as described above and with $R_2=H$, $R_3=$p-hydroxyphenyl-$CH_2$-, $R_4=H$. FAB mass spectrum: obs. 561 (m+1). HPLC retention time: 19.5 min.

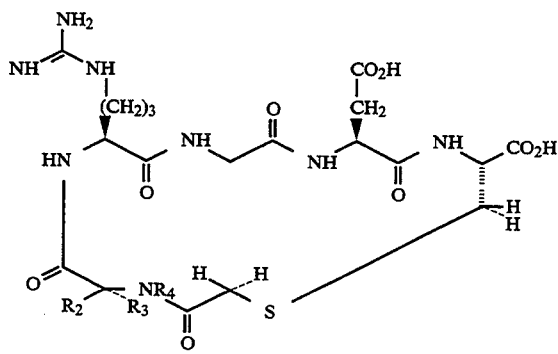

VII

Example 12

A compound of Formula VII as described above and with $R_2+R_4=(CH_2)_3$, $R_3=H$. FAB mass spectrum: obs. 587 (m+1). HPLC retention time: 17.5 min.

Example 13

A compound of Formula VII as described above and with $R_2=H$, $R_3+R_4=(CH_2)_3$. Amino acid analysis: SocarboxymethylCys, 0.91; Pro, 1.06; Arg, 1.00; Gly, 1.01; Asp 1.08; Cys, 0.12.

Example 14

A compound of Formula VII as described above and with $R_2$=4-imidazolyl-$CH_2$-, $R_3=H$, $R_4=H$. FAB mass spectrum: obs. 627 (m+1). HPLC retention time: 8.0 min.

Example 15

A compound of Formula VII as described above and with $R_2=H$, $R_3$=4-imidazolyl-$CH_2$-, $R_4=H$.

Using the method described in Example 3, the compounds listed in Examples 16–21 may be prepared. The compounds are depicted by Formula VIII and are derivatives of Formula I wherein $R_1=R_9=OH$, $R_2=R_3=R_4=R_7=R_8=R_{14}=H$, $X=S$, $n=3$, $m=1$, the chirality of the asymmetric carbon atoms bearing the $(CH_2)_n$ and $(CH_2)_m$ are each S, the chirality of the asymmetric carbon atom bearing the $R_1$ substituent is R and the remaining substituents are as described in the following individual examples. Crude products are purified using HPLC as described in Example 2.

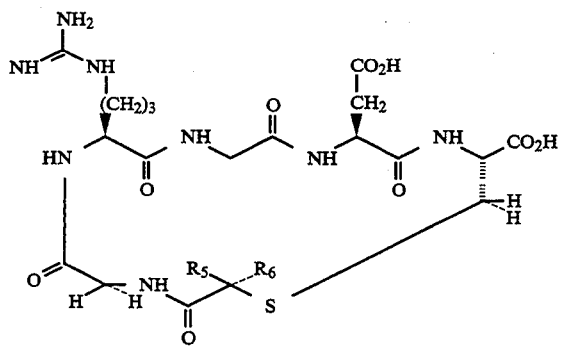

Example 16

A pair of isomeric compounds of Formula VIII as described above with $R_5=H$ and $R_6=C_2H_5$ or $R_5=C_2H_5$ and $R_6=H$. Isomer A. FAB mass spectrum: 575 (m+1). HPLC retention time: 15.5 min. Isomer B. FAB mass spectrum: 575 (m+1). HPLC retention time: 17.5 min.

Example 17

A pair of isomeric compounds of Formula VIII as described above with $R_5=H$ and $R_6$=n-$C_3H_7$ or $R_5$=n-$C_3H_7$ and $R_6=H$. Isomer A. FAB mass spectrum: obs. 589 (m+1). HPLC retention time: 21.5 min. Isomer B. FAB mass spectrum: obs. 589 (m+1). HPLC retention time: 23.5 min.

Example 18

A pair of isomeric compounds of Formula VIII as described above with $R_5=H$ and $R_6$=phenyl or $R_5$=phenyl and $R_6=H$. Isomer A. FAB mass spectrum: 623 (m+1). HPLC retention time: 26 min. Isomer B. FAB mass spectrum: 623 (m+1). HPLC retention time: 28 min.

Example 19

A compound of Formula VIII as described above with $R_5=H$ and $R_5=CH_3$ or $R_5=CH_3$ and $R_6=H$. FAB mass spectrum: 561 (m+1). HPLC retention time: 12 min.

Example 20

A compound of Formula VIII wherein $R_1=R_9=OH$, $R_2=R_3=R_4=R_5=R_6=R_7=R_8=R_{14}=H$, $n=3$, $m=1$, $X=S$, and the asymmetric carbon atom bearing the $COR_1$ group is of the S configuration may be prepared following the procedures outined in Examples 1 and 2 when D-cysteine is used in place of L-cysteine.

Example 21

A compound of Formula VIII wherein $R_1=R_9=OH$, $R_2=R_2=R_3=R_4=R_5=R_6=R_{14}=H$, $R_7=R_8=CH_3$, $n=3$, $m=1$, $X=S$ and the asymmetric carbon atom bearing the $COR_1$ group is of the R configuration may be prepared following the procedures outined in Examples 1 and 2 when D-penicillamine is used in place of L-cysteine.

Example 22

N-(N-t-Butoxycarbonyl(g-p-toluenesulfonyl)arginyl) glycine

N-t-Butoxycarbonyl-g-p-toluenesulfonylarginine (10 mmoles), benzotriazol-1-yloxytris(dimethylamino)phosphonium hexafluorophosphate (BOP, 10 mmoles), ethyl glycinate hydrochloride (13 mmoles) and N-methylmorpholine (50 mmoles) are stirred in a mixture of dichloromethane and dimethylacetamide (1:1, 50 ml) for 2 hr at room temperature. At the end of the reaction time the mixture is acidified with acetic acid, concentrated in vacuo, and the residue taken up in ethyl acetate. The resulting solution is washed with 10% citric acid (3 times), water (2 times), saturated sodium bicarbonate (3 times), water (2 times) and brine (2 times). The organic solution is dried over magnesium sulfate, filtered, dried and concentrated to afford the crude ethyl ester of the title compound. Crystalline material can be obtained from ethyl acetate-hexane mixtures.

The dipeptide ethyl ester (10 mmoles) is treated with 10.5 mmoles of sodium hydroxide in ethanol and water (4:1, 50 ml) for 1 hr at room temperature. Water (100 ml) is added and the mixture concentrated to ca 50 ml, acidified with citric acid, and extracted with ethyl acetate. After drying the extract over magnesium sulfate, concentration affords the desired title compound. It may be recrystallized from ethyl acetate-hexane mixtures.

Example 23

VIII

N-(N-t-butoxycarbonyl(beta-cyclohexyl ester)aspartyl) cysteine (S-4-methylbenzyl)benzyl ester

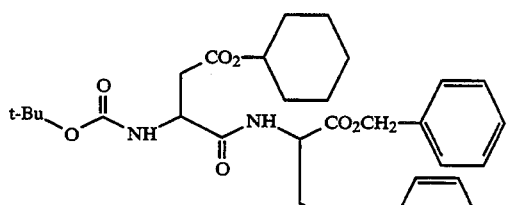

N-t-Butoxycarbonyl(beta-cyclohexyl ester)aspartic acid (10 mmole), BOP reagent (10 mmole), and N-methylmorpholine (15 mmole) are stirred in dimethylacetamide (50 ml) at room temperature for 10 min. To the resulting solution is added a solution of cysteine(S-4-methylbenzyl) benzyl ester trifluoroacetate (10 mmole) and N-methylmorpholine (15 mmole) in dimethylacetamide (15 ml). The resulting reaction mixture is stirred overnight at room temperature. The solvent is then removed in vacuo and the reaction residue worked up as described in Example 22 to afford the desired title compound.

Example 24

N-(N-(N-(N-t-Butoxycarbonyl(g-p-toluenesulfonyl)arginyl) glycinyl)aspartyl(beta-cyclohexyl ester))cysteine(S-4-methylbenzyl) benzyl ester.

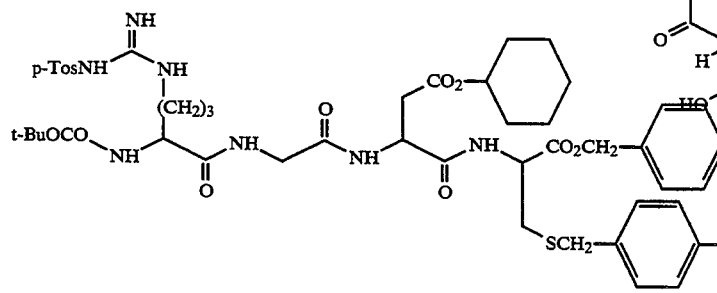

N-(N-t-butoxycarbonyl(beta-cyclohexyl ester)aspartyl) cysteine (S-4-methylbenzyl) benzyl ester from Example 23 (10 mmole) is treated with trifluoroacetic acid in dichloromethane (1:1, 200 ml) for 40 min at room temperature and then concentrated. The resulting solid is washed with ether and dried.

The above solid (10 mmole), BOP reagent (10 mmole), N-methylmorpholine (40 mmole) and N-(N-t-Butoxycarbonyl(g-p-toluenesulfonyl)arginyl)glycine from Example 22 (10 mmole) are stirred in dimethylacetamide (50 ml) for 4 hr. After the reaction time is up, the reaction solution is concentrated and the residue taken up in ethyl acetate and worked up as described in Example 22. The crude product thus obtained is recrystallized from chloroform-hexane.

Example 25

N-(N-(N-(N-(N-t-Butoxycarbonyl(O-benzyl)-d-threonyl)(g-p-toluenesulfonyl)arginyl) glycinyl)aspartyl(beta-cyclohexyl ester))cysteine(S-4-methylbenzyl) benzyl ester.

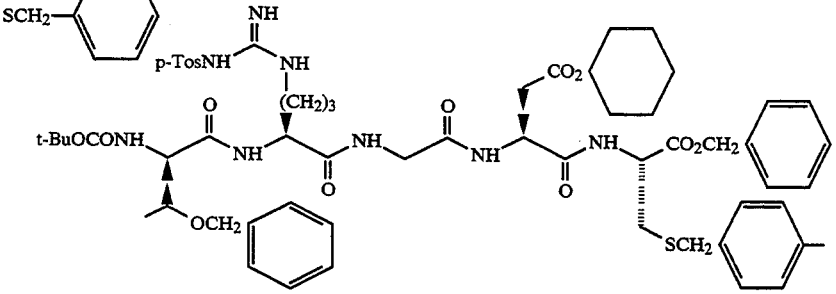

The t-butoxycarbonyl group is removed from N-(N-(N-(N-t-butoxycarbonyl(g-p-toluenesulfonyl)arginyl) glycinyl)aspartyl(beta-cyclohexyl ester))cysteine(S-4-methylbenzyl) benzyl ester using the procedure described in Example 24 to afford the trifluoroacetate salt of the tetrapeptide.

The above salt is coupled with N-t-butoxycarbonyl-(O-benzyl)-d-threonine using the procedure described in Example 24. The desired title compound is isolated after workup as described above.

Example 26

Cyclo-S-acetyl-(d-Thr)-Arg-Gly-Asp-Cys-OH

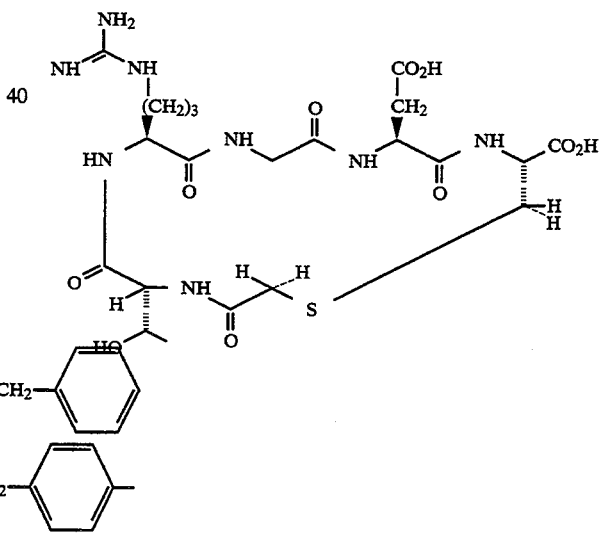

The t-butoxycarbonyl group is removed from N-(N-(N-(N-t-Butoxycarbonyl(O-benzyl)-d-threonyl)(g-p-toluenesulfonyl)arginyl) glycinyl)aspartyl(beta-cyclohexyl ester))cysteine(S-4methylbenzyl) benzyl ester using the procedure described in Example 24 to afford the trifluoroacetate salt of the pentapeptide.

Bromoacetic acid (4 mmole) and dicyclohexylcxarbodiimide (2 mmole) are stirred together in 5 ml of dichloromethane for 10 min. The solution is filtered and added to the pentapeptide trifluoroacetate prepared above (1 mmole) and N-methylmorpholine (3 mmole) in dimethylacetamide (5 ml). After stirring for 1 hr at room temperature the reaction is concentrated in vacuo and the residue taken up in ethyl acetate and worked up as described in Example 22. The residue isolated from the ethyl acetate solution is treated directly with a mixture of hydrogen fluoride, anisole and methylethyl sulfide (90:5:5) at 0 C for 1 hr. After removal of the hydrogen fluoride the crude material is dissolved in 10% acetic acid and lyophilized. The isolated powder is then dissolved in water at a concentration of 1 mg/ml and the pH adjusted to 7.3 with ammonium hydroxide. After stirring at ambient temperature for 4 hr the reaction solution is loaded onto a DEAE 52 cellulose column equilibrated in 5 mM ammonium acetate at pH 7.3. The desired title compound is eluted with 45 mM ammonium acetate at pH 7.3. The fractions containing the desired cyclized peptide are desalted immediately by acidification to pH 4 with acetic acid and chromatography over a C-18 reverse phase column. The loaded column is first washed with 0.1% aqueous trifluoroacetic acid followed by linear gradient with 0.1% trifluoroacetic acid in acetonitrile. The purified peptide, after lyophilization, is identical with the product described in Example 7.

Using the methods described in Examples 22–26, the compounds described in Examples 27–41 may be prepared. The compounds are depicted by Formula IX and are derivatives of Formula I wherein $R_5=R_6=R_7=R_8=R_{14}=H$, $X=S$, $n=3$, $m=1$, the chirality of the assymmetric carbon atoms bearing the $(CH_2)_n$ and $(CH_2)_m$ chains are each S, the chirality of the asymmetric carbon atom bearing the $COR_1$ substituent is R and the remaining substituents are as described in the following Examples.

Example 27

A compound of Formula IX as described above with $R_1$=ethoxy, $R_9$=OH, $R_2$=H, $R_3$=CH$_3$CH(OH)—, $R_4$=H. The hydroxy bearing carbon atom has the same configuration as occurs in D-threonine.

This compound may be prepared using the corresponding ethyl ester derivative of cysteine in place of the benzyl ester derivative in Example 23.

Example 28

A compound of Formula IX as described above with $R_1$=OH, $R_9$=ethoxy, $R_2$=H, $R_3$=CH$_3$CH(OH)-, $R_4$=H. The hydroxy bearing carbon atom has the same configuration as occurs in D-threonine.

This compound may be prepared using the corresponding beta-ethyl ester derivative of aspartic acid in place of the cyclohexyl ester derivative in Example 23.

Example 29

A compound of Formula IX as described above with $R_1$=ethoxy, $R_9$=ethoxy, $R_2$=H, $R_3$=CH$_3$CH(OH)-, $R_4$=H. The hydroxy bearing carbon atom has the same configuration as occurs in D-threonine.

This compound may be prepared using the corresponding beta-ethyl ester derivative of aspartic acid in place of the cyclohexyl ester derivative and the corresponding ethyl ester derivative of cysteine in place of the benzyl ester derivative in Example 23.

Example 30

A compound of Formula IX as described above with $R_1$=ethoxy, $R_9$=OH, $R_3+R_4=(CH_2)3$, and $R_2$=H.

This compound may be prepared using the corresponding ethyl ester derivative of cysteine in place of the benzyl ester derivative in Example 23 and N-t-butoxycarbonyl-D-proline in place of the D-threonine derivative in Example 25.

Example 31

A compound of Formula IX as described above with $R_1$=OH, $R_9$=ethoxy, $R_3+R_4=(CH_2)3$, and $R_2$=H.

This compound may be prepared using the corresponding beta-ethyl ester derivative of aspartic acid in place of the cyclohexyl ester derivative in Example 23 and N-t-butoxycarbonyl-D-proline in place of the D-threonine derivative in Example 25.

Example 32

A compound of Formula IX as described above with $R_1$=ethoxy, $R_9$=ethoxy, $R_3+R_4=(CH_2)3$, and $R_2$=H.

This compound may be prepared using the corresponding beta-ethyl ester derivative of aspartic acid in place of the cyclohexyl ester derivative and the corresponding ethyl ester derivative of cysteine in place of the benzyl ester derivative in Example 23 and N-t-butoxycarbonyl-D-proline in place of the D-threonine derivative in Example 25.

Example 33

A compound of Formula IX as described above with $R_1$=ethoxy, $R_9$=OH, $R_3$=p-hydroxyphenylmethyl, $R_4$=H, and $R_2$=H.

This compound may be prepared using the corresponding ethyl ester derivative of cysteine in place of the benzyl ester derivative in Example 23 and N-t-butoxycarbonyl-O-benzyl-D-tyrosine in place of the D-threonine derivative in Example 25.

Example 34

A compound of Formula IX as described above with $R_1$=OH, $R_9$=ethoxy, $R_3$=p-hydroxyphenylmethyl, $R_4$=H, and $R_2$=H.

This compound may be prepared using the corresponding beta-ethyl ester derivative of aspartic acid in place of the cyclohexyl ester derivative in Example 23 and N-t-butoxycarbonyl-O-benzyl-D-tyrosine in place of the D-threonine derivative in Example 25.

Example 35

A compound of Formula IX as described above with $R_1$=ethoxy, $R_9$=ethoxy, $R_3$=p-hydroxyphenylmethyl, $R_4$=H, and $R_2$=H.

This compound may be prepared using the corresponding beta-ethyl ester derivative of aspartic acid in place of the cyclohexyl ester derivative and the corresponding ethyl ester derivative of cysteine in place of the benzyl ester derivative in Example 23 and N-t-butoxycarbonyl-O-benzyl-D-tyrosine in place of the D-threonine derivative in Example 25.

Example 36

A compound of Formula IX as described above with $R_1$=ethoxy, $R_9$=OH, $R_3$=H, $R_4$=H, and $R_2$=H.

This compound may be prepared using the corresponding ethyl ester derivative of cysteine in place of the benzyl ester derivative in Example 23 and N-t-butoxycarbonylglycine in place of the D-threonine derivative in Example 25.

Example 37

A compound of Formula IX as described above with $R_1$=OH, $R_9$=ethoxy, $R_3$=H, $R_4$=H, and $R_2$=H.

This compound may be prepared using the corresponding beta-ethyl ester derivative of aspartic acid in place of the cyclohexyl ester derivative in Example 23 and N-t-butoxycarbonylglycine in place of the D-threonine derivative in Example 25.

Example 38

A compound of Formula IX as described above with $R_1$=ethoxy, $R_9$=ethoxy, $R_3$=H, $R_4$=H, and $R_2$=H.

This compound may be prepared using the corresponding beta-ethyl ester derivative of aspartic acid in place of the cyclohexyl ester derivative and the corresponding ethyl ester derivative of cysteine in place of the benzyl ester derivative in Example 23 and N-t-butoxycarbonylglycine in place of the D-threonine derivative in Example 25.

Example 39

A compound of Formula IX as described above with $R_1$=ethoxy, $R_9$=OH, $R_3$=CH$_3$, $R_4$=H, and $R_2$=H.

This compound may be prepared using the corresponding ethyl ester derivative of cysteine in place of the benzyl ester derivative in Example 23 and N-t-butoxycarbonyl-D-alanine in place of the D-threonine derivative in Example 25.

Example 40

A compound of Formula IX as described above with $R_1$=OH, $R_9$=ethoxy, $R_3$=CH$_3$, $R_4$=H, and $R_2$=H.

This compound may be prepared using the corresponding beta-ethyl ester derivative of aspartic acid in place of the cyclohexyl ester derivative in Example 23 and N-t-butoxycarbonyl-D-alanine in place of the D-threonine derivative in Example 25.

Example 41

A compound of Formula IX as described above with $R_1$=ethoxy, $R_9$=ethoxy, $R_3$=CH$_3$, $R_4$=H, and $R_2$=H.

This compound may be prepared using the corresponding beta-ethyl ester derivative of aspartic acid in place of the cyclohexyl ester derivative and the corresponding ethyl ester derivative of cysteine in place of the benzyl ester derivative in Example 23 and N-t-butoxycarbonyl-D-alanine in place of the D-threonine derivative in Example 25.

Example 42

Inhibition of fibrinogen binding to GP llblIla

Microtiter plates are coated with fibrinogen (10 ug/ml) and then blocked with TACTS buffer containing 0.5% BSA. (TACTS buffer contains 20mM Tris. HCl, pH 7.5, 0.02% sodium azide, 2 mM calcium chloride, 0.05% Tween 20, 150 mM sodium chloride.) The plate is washed with phosphate buffered saline containing 0.01% Tween 20 and a dilution of the sample to be determined added, followed by addition of solubilized llblIla receptor (40 ug/ml) in TACTS, 0.5% BSA. After incubation, the plate is washed and murine monoclonal anti-platelet antibody AP3 (1 ug/ml) added. After another wash goat and anti-mouse IgG conjugated to horseradish peroxidase is added. A final wash is performed and developing reagent buffer (10 mg o-phenylenediamine dihydrochloride, 0.0212% hydrogen peroxide, 0.22 mM citrate, 50 mM phosphate, pH 5.0) is added and then incubated until color developed. The reaction is stopped with 1N sulfuric acid and the absorbance at 492 nm is recorded. The smaller the ratio in Table I, the more actively the test compound inhibits fibrinogen binding to GP llblIla.

TABLE 1

In Vitro Activities of Cyclic Peptides in GP IIbIIIa Receptor Assay for Inhibition of Fibrinogen Binding

| Compound | Refer to[1] | Ratio[2] |
|---|---|---|
| Gly—Arg—Gly—Asp—Val | | 1 |
| Arg—Gly—Asp—Ser | | >20 |
| Arg—Gly—Asp—Val | | 3 |
| cyclo-S-acetyl-Gly—Arg—Gly—Asp—Cys—OH | Ex. 2 | 0.14 |
| cyclo-S-acetyl-(dAsn)-Arg—Gly—Asp—Cys—OH | Ex. 5 | 0.14 |
| cyclo-S-acetyl-Thr—Arg—Gly—Asp—Cys—OH | Ex. 6 | 0.46 |
| cyclo-S-acetyl-(dThr)-Arg—Gly—Asp—Cys—OH | Ex. 7 | 0.07 |
| cyclo-S-acetyl-Ala—Arg—Gly—Asp—Cys—OH | Ex. 8 | 0.5 |
| cyclo-S-acetyl-(dAla)-Arg—Gly—Asp—Cys—OH | Ex. 9 | 0.13 |
| cyclo-S-acetyl-Tyr—Arg—Gly—Asp—Cys—OH | Ex. 10 | 0.38 |
| cyclo-S-acetyl-(dTyr)-Arg—Gly—Asp—Cys—OH | Ex. 11 | 0.09 |
| cyclo-S-acetyl-Pro—Arg—Gly—Asp—Cys—OH | Ex. 12 | 0.46 |
| cyclo-S-acetyl-(dPro)-Arg—Gly—Asp—Cys—OH | Ex. 13 | 0.05 |
| cyclo-S-Phenylacetyl-Gly—Arg—Gly—Asp—Cys—OH | Ex. 18 | 0.6 |
| cyclo-S-Phenylacetyl-Gly—Arg—Gly—Asp—Cys—OH | Ex. 18 | 0.08 |

[1]Example which describes the preparation of the compound
[2]Ratio of IC$_{50}$ of test compound to IC$_{50}$ of Gly—Arg—Gly—Asp—Val.
The IC$_{50}$ of Gly—Arg—Gly—Asp—Val is typically in the range of 20–40 nM.

Example 43

Inhibition of platelet aggregation.

Fifty milliliters of whole human blood (9 parts) is drawn on 3.6% sodium citrate (1 part) from a donor who has not taken aspirin or related medications for at least two weeks. The blood is centrifuged at 160×g for 10 min at 22° C. and then allowed to stand for 5 min after which the PRP is decanted. Platelet poor plasma (PPP) is isolated from the remaining blood after centrifugation at 2000×g for 25 min. The platelet count of the PRP was diluted to ca. 300000 per microliter with PPP.

A 225 uL aliquot of PRP plus 25 uL of either a dilution of the test sample or a control (PBS) is incubated for 5 min in a Chrono-log Whole Blood Aggregometer at 25° C. Adenosine diphosphate (ADP, 8 uM) is added and the platelet aggregation recorded. The results of this test are recorded in Table 2.

TABLE 2

In Vitro Platelet Aggregation Inhibition by Cyclic Peptides

| Compound | Refer to[1] | IC$_{50}$ (uM) |
|---|---|---|
| Gly—Arg—Gly—Asp—Val | | 75 |
| cyclo-S-acetyl-Gly—Arg—Gly—Asp—Cys—OH | Ex. 2 | 8 |
| cyclo-S-acetyl-(dThr)-Arg—Gly—Asp—Cys—OH | Ex. 7 | 0.8 |
| cyclo-S-acetyl-(dAla)-Arg—Gly—Asp—Cys—OH | Ex. 9 | 3.0 |
| cyclo-S-acetyl-(dTyr)-Arg—Gly—Asp—Cys—OH | Ex. 11 | 0.8 |
| cyclo-S-acetyl-(dPro)-Arg—Gly—Asp—Cys—OH | Ex. 13 | 2 |
| cyclo-S-Phenylacetyl-Gly—Arg—Gly—Asp—Cys—OH | Ex. 18 | 3 |

[1]Example which describes the preparation of the compound

In view of the efficacy of these cyclic polypeptides as inhibitors of fibrinogen binding to GP IIbIIIa, and the feasibility as demonstrated herein of producing these cyclic polypeptides, the present invention may have application in the treatment of a large group of disorders associated with, or characterized by, a hyperthrombotic state. Representative of such disorders are genetic or aquired deficiencies of factors which normally prevent a hyperthrombotic state; medical procedures such as angioplasty and thrombolytic therapy; mechanical obstructions to blood flow, such as tumor masses, prosthetic synthetic cardiac valves, and extracorporeal perfusion devices; atherosclerosis; and coronary artery disease.

The present invention has of necessity been discussed herein by reference to certain specific methods and materials. It is to be understood that the discussion of these specific methods and materials in no way constitutes any limitation on the scope of the present invention, which extends to any and all alternative materials and methods suitable for accomplishing the objectives of the present invention.

What is claimed is:

1. A compound of the formula:

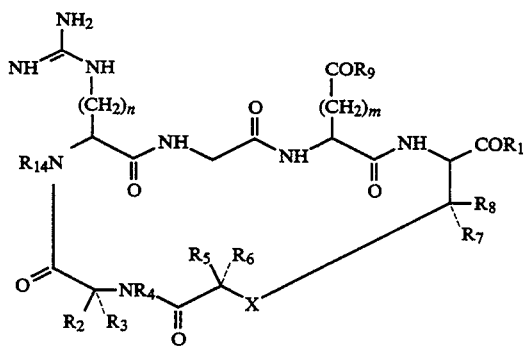

wherein $R_1$ and $R_9$ are the same or different and are selected from the group consisting of hydroxy, $C_1$–$C_8$ alkoxy, $C_2$–$C_{12}$ alkenoxy, $C_6$–$C_{12}$ aryloxy, di-$C_1$–$C_8$ alkylamino-$C_1$–$C_8$-alkoxy, acylamino-$C_1$–$C_8$-alkoxy selected from the group acetylaminoethoxy, nicotinoylaminoethoxy, and succinamidoethoxy, pivaloyloxyethoxy, $C_6$–$C_{12}$ aryl-$C_1$–$C_8$-alkoxy, hydroxy-$C_2$–$C_8$-alkoxy, dihydroxy-$C_3$–$C_8$-alkoxy, and a substituted heteroatom $NR_{10}R_{11}$;

$R_{10}$, $R_{11}$ and $R_{14}$ are the same or different and are selected from the group consisting of hydrogen, $C_1$–$C_8$-alkyl, $C_3$–$C_8$-alkenyl, $C_6$–$C_{12}$-aryl, and $C_6$–$C_{12}$-aryl-$C_1$–$C_8$-alkyl; $R_2$, $R_3$, $R_5$, $R_6$, $R_7$, $R_8$ are the same or different and are selected from the group consisting of hydrogen, $C_1$–$C_{12}$ alkyl which include branched and unsaturated alkyl groups, substituted $C_1$–$C_8$ alkyl where the substituent(s) are selected from the group consisting of halo, $C_1$–$C_8$ alkoxy, $C_6$–$C_{12}$ aryloxy, isothioureido, ureido, amino, $C_1$–$C_8$ alkylamino, di-$C_1$–$C_8$ alkylamino, hydroxy, amino-$C_2$–$C_8$ alkylthio, amino-$C_2$–$C_8$ alkoxy, acetamido, benzamido, $C_6$–$C_{12}$ arylamino, guanidino, phthalimido, mercapto, $C_1$–$C_8$ alkylthio, $C_6$–$C_{12}$ arylthio, carboxy, carboxamide, carbo-$C_1$–$C_8$ alkoxy, $C_6$–$C_{12}$ aryl-$C_1$–$C_8$ alkyl, $C_6$–$C_{12}$ aryl-$C_2$–$C_8$ alkenyl, aromatic heterocyclo-$C_1$–$C_8$ alkyl, aromatic heterocyclo-$C_2$–$C_8$ alkenyl where the heterocyclic groups have 5–10 ring atoms and contain up to two O, N, or S heteroatoms, substituted $C_6$–$C_{12}$-aryl-$C_1$–$C_8$alkyl and substituted aromatic heterocyclo-$C_1$–$C_8$ alkyl where the substituent(s) are selected from the group consisting of halo, dihalo, $C_1$–$C_8$ alkyl, hydroxy, $C_1$–$C_8$ alkoxy, amino, guanidino, isothioureido, ureido, aminoC$_1$–$C_8$alkyl, phenyloxy, acetamido, benzamido, di-$C_1$–$C_8$ alkylamino, $C_1$–$C_8$ alkylamino, carboxyl, $C_6$–$C_{12}$ aroyl, $C_1$–$C_8$ alkanoyl and the heterocyclic groups as defined above, optionally either $R_5$ or $R_6$ is phenyl;

$R_4$ is selected from the group consisting of hydrogen, $C_1$–$C_8$ alkyl, $C_3$–$C_{10}$ cycloalkyl, $C_6$–$C_{12}$ aryl, and $C_6$–$C_{12}$ aryl-$C_1$–$C_8$-alkyl;

$R_2$ and $R_3$, $R_5$ and $R_6$, or $R_7$ and $R_8$ maybe joined together to form a ring of three to six carbon atoms or a ring of two to five carbon atoms and one O or S heteroatom or substituted heteroatom $NR_{12}$;

$R_{12}$ is selected from the group consisting of $C_1$–$C_8$-alkyl, $C_3$–$C_8$-alkenyl, $C_6$–$C_{12}$-aryl, $C_6$–$C_{12}$-aryl-$C_1$–$C_8$-alkyl, $C_1$–$C_8$ alkanoyl, and $C_6$–$C_{12}$ aroyl;

$R_2$ or $R_3$ may be joined with $R_4$ to form an alkylene bridge of from two to five carbon atoms or an alkylene bridge of from two to four carbon atoms and one O or S heteroatom;

X is an O or S heteroatom or S heteroatom bearing one or two O heteroatoms or substituted $NR_{13}$ heteroatom or a methylene group;

$R_{13}$ is selected from the group consisting of hydrogen, $C_1$–$C_8$-alkyl, $C_3$–$C_8$-alkenyl, $C_6$–$C_{12}$-aryl, $C_6$–$C_{12}$-aryl-$C_1$–$C_8$-alkyl, $C_1$–$C_8$ alkanoyl, and $C_6$–$C_{12}$ aroyl;

n is an integer from 1 to 6;

m is 1;

and the pharmaceutically acceptable salts thereof, provided that the chirality of the carbon atom bearing the (CH$_2$)m sidechain is S.

2. A compound of the formula:

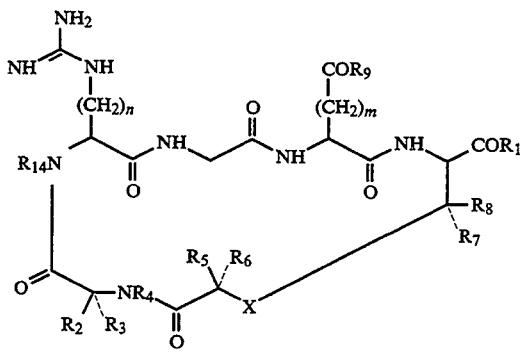

wherein
- $R_1$ and $R_9$ are the same or different and are selected from the group consisting of hydroxy, $C_1$-$C_8$ alkoxy, and $C_6$-$C_{12}$ aryl-$C_1$-$C_8$ alkoxy;
- $R_2$, $R_3$, $R_5$, $R_6$, $R_7$, $R_8$, are the same or different and are selected from the group consisting of hydrogen, $C_1$-$C_6$ alkyl which include branched and unsaturated alkyl groups substituted $C_1$-$C_6$ alkyl where the substituent(s) are selected from the group consisting of isothioureido, ureido, amino, $C_1$-$C_4$ alkylamino di-$C_1$-$C_4$ alkylamino, hydroxy, acetamido, benzamido, $C_6$-$C_{12}$ arylamino, guanidino, mercapto, $C_1$-$C_8$ alkylthio, carboxy, carboxamide, carbo-$C_1$-$C_4$ alkoxy, $C_6$-$C_{12}$ aryl-$C_1$-$C_8$ alkyl, aromatic heterocyclo-$C_1$-$C_8$ alkyl where the heterocyclic groups have 5–10 ring atoms and contain up to two O, N, or S heteroatoms substituted $C_6$-$C_{12}$ aryl-$C_1$-$C_8$ alkyl, and substituted aromatic heterocyclo-$C_1$-$C_8$ alkyl where the substituent(s) are selected from the group consisting of halo, dihalo, $C_1$-$C_4$ alkyl, hydroxy, $C_1$-$C_4$ alkoxy, amino, guanidino, isothioureido, ureido, amino-$C_1$-$C_4$ alkyl, acetamido, benzamido, di-$C_1$-$C_4$ alkylamino, $C_1$-$C_4$ alkylamino, carboxyl, $C_6$-$C_{12}$ aroyl, $C_1$-$C_4$ alkanoyl, and the heterocyclic groups are as defined above; optionally either $R_5$ or $R_6$ is phenyl;
- $R_4$ is hydrogen or may be joined with $R_2$ or $R_3$ to form an alkylene bridge of from two to five carbon atoms or an alkylene bridge of from two to four carbon atoms and one O or S heteroatom;
- $R_2$ and $R_3$, $R_5$ and $R_6$, or $R_7$ and $R_8$ may be joined together to form a ring of three to six carbon atoms or a ring of two to five carbon atoms and one O or S heteroatom or substituted heteroatom $NR_{12}$;
- $R_{12}$ is selected from the group consisting of $C_1$-$C_4$ alkyl, $C_6$-$C_{12}$-aryl, $C_6$-$C_{12}$-aryl-$C_1$-$C_4$ alkanoyl, and $C_6$-$C_{12}$ aroyl;
- X is an O or S heteroatom bearing one or two O heteroatoms or substituted $NR_{13}$ heteroatom or a methylene group;
- $R_{13}$ is selected from the group consisting of hydrogen, $C_1$-$C_4$-alkyl, $C_6$-$C_{12}$-aryl, $C_6$-$C_{12}$-aryl-$C_1$-$C_4$-alkyl, $C_1$-$C_4$ alkanoyl, and $C_6$-$C_{12}$ aroyl;
- $R_{14}$ is selected from the group, consisting of hydrogen, $C_1$-$C_4$-alkyl, $C_6$-$C_{12}$-aryl, and $C_6$-$C_{12}$-aryl-$C_1$-$C_4$-alkyl,
- n is an integer from 1 to 6;
- m is 1;

and the pharmaceutically acceptable salts thereof, provided that the chirality of the carbon atoms bearing the $(CH_2)_n$ sidechain and the $(CH_2)_m$ sidechain is S.

3. A compound of the formula:

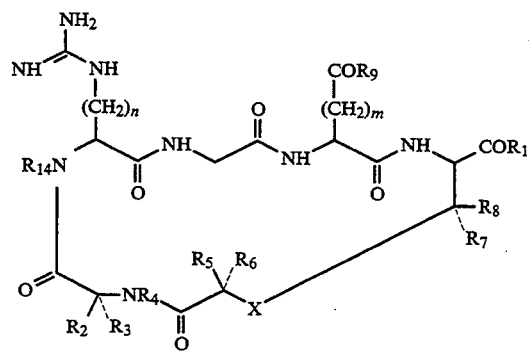

wherein
- $R_1$ and $R_9$ are the same or different and are selected from the group consisting of hydroxy, $C_1$-$C_4$ alkoxy and $C_6$-$C_{12}$ aryl-$C_1$-$C_4$ alkoxy: $R_2$, $R_3$, $R_5$, $R_6$, $R_7$, $R_8$ are the same or different and are selected from the group consisting of hydrogen, $C_1$-$C_6$ alkyl which include branched and unsaturated alkyl groups substituted $C_1$-$C_6$ alkyl where the substituent(s) are selected from the group consisting of amino, $C_1$-$C_4$ alkylamino, di-$C_1$-$C_4$ alkylamino, hydroxy, acetamido, benzamido, $C_6$-$C_{12}$ arylamino, guanidino, mercapto, $C_1$-$C_8$ alkylthio, carboxy, carboxamide, carbo-$C_1$-$C_4$ alkoxy, $C_6$-$C_{12}$ aryl-$C_1$-$C_4$ alkyl aromatic heterocyclo-$C_1$-$C_4$ where the heterocyclic groups have 5–10 ring atoms and contain up to two O, N, or S heteroatoms, substituted $C_6$-$C_{12}$ aryl-$C_1$-$C_4$ alkyl and substituted aromatic heterocyclo-$C_1$-$C_4$ alkyl where the substituent(s) are selected from the group consisting of halo, dihalo, $C_1$-$C_4$ alkyl, hydroxy, $C_1$-$C_4$ alkoxy, amino, guanidino, amino-$C_1$-$C_4$ alkyl, acetamido, benzamido, di-$C_1$-$C_4$ alkylamino, $C_1$-$C_4$ alkylamino, carboxyl, $C_6$-$C_{12}$ aroyl, $C_1$-$C_4$ alkanoyl, and the heterocyclic groups are as defined above, optionally either $R_5$ or $R_6$ is phenyl;
- $R_4$ is hydrogen or may be joined with $R_2$ or $R_3$ to form an alkylene bridge of from two to five carbon atoms or an alkylene bridge of from two to four carbon atoms and one O or S heteroatom;
- $R_2$ and $R_3$, $R_5$ and $R_6$, or $R_7$ and $R_8$ may be joined together to form a ring of three to six carbon atoms or a ring of two to five carbon atoms and one O or S heteroatom or substituted heteroatom $NR_{12}$;
- $R_{12}$ is selected from the group consisting of $C_1$-$C_4$ alkyl, $C_6$-$C_{12}$-aryl, $C_6$-$C_{12}$-aryl-$C_1$-$C_1$-$C_4$ alkanoyl, and $C_6$-$C_{12}$ aroyl;
- X is an O or S heteroatom or S heteroatom bearing one or two heteroatoms or substituted $NR_{13}$ heteroatom or a methylene group;
- $R_{13}$ is selected from the group consisting of hydrogen, $C_1$-$C_4$ alkyl, $C_6$-$C_{12}$-aryl-$C_1$-$C_4$ alkanoyl, and $C_6$-$C_{12}$ aroyl;
- $R_{14}$ is selected from the group consisting of hydrogen, $C_1$-$C_4$-alkyl, $C_6$-$C_{12}$-aryl, and $C_6$-$C_{12}$-aryl-$C_1$-$C_4$-alkyl;
- n is an integer from 2 to 4;
- m is 1;

and the pharmaceutically acceptable salts thereof provided that the chirality of the carbon atoms bearing the $(CH_2)_n$ sidechain and the $(CH_2)_m$ sidechain is S and the chirality of the carbon atom bearing substituents $R_2$ and $R_3$ corresponds to that of a D amino acid.

4. A compound of the formula:

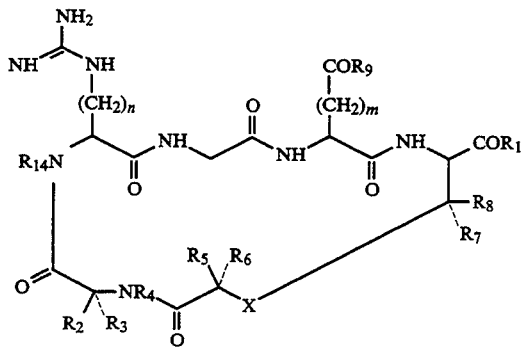

wherein $R_1$ and $R_9$ are the same or different and are selected from the group consisting of hydroxy, $C_1$-$C_4$ alkoxy, and benzyloxy;

$R_2$ or $R_3$ is hydrogen and the remaining substituent is selected from the group consisting of hydrogen, $C_1$-$C_6$ alkyl which includes branched alkyl groups, and substituted $C_1$-$C_6$ alkyl where the substituent are selected from the group consisting of amino, hydroxy, mercapto, carboxy, carboxamide, guanidino, phenyl, hydroxyphenyl, indolyl, and imidazolyl;

$R_5$ or $R_6$ is hydrogen and the remaining substituent is selected from the group consisting of hydrogen, phenyl, $C_1$-$C_6$ alkyl which includes branched alkyl groups, and substituted $C_1$-$C_6$ alkyl where the substituents are selected from the group Consisting of amino, hydroxy, mercapto, carboxy, carboxamide, guanidino, phenyl, hydroxyphenyl, indolyl, and imidazolyl;

$R_7$ or $R_8$ is hydrogen or $C_1$-$C_6$ alkyl which includes branched alkyl groups and the remaining substituent is selected from the group consisting of hydrogen, $C_1$-$C_6$ alkyl which includes branched alkyl groups, and substituted $C_1$-$C_6$ alkyl where the substituent can be amino, hydroxy, mercapto, carboxy, carboxamide, guanidino, phenyl, hydroxyphenyl, indolyl, and imidazolyl;

$R_4$ is hydrogen or may be joined with $R_2$ or $R_3$ to form an alkylene bridge of three or four carbon atoms or an alkylene bridge of two carbon atoms and one S heteroatom;

X is an or S heteroatom or an S heteroatom bearing one or two O heteroatoms;

$R_{14}$ is selected from the group consisting of hydrogen, $C_1$-$C_4$-alkyl, $C_6$-$C_{12}$-aryl, and $C_6$-$C_{12}$-aryl-$C_1$-$C_4$-alkyl;

n is 3;

m is 1;

and the pharmaceutically acceptable salts thereof, provided that the chirality of the carbon atoms bearing the $(CH_2)_n$ sidechain and the $(CH_2)_m$ sidechain is S, the chirality of the carbon atom bearing the $COR_1$ group is R, and the chirality of the carbon atom bearing substituents $R_2$ and $R_3$ corresponds to that of a D amino acid.

5. A compound of claim 4 wherein $R_1=R_9=OH$, $R_2$-$R_8$ and $R_{14}$ are all H, and X=S.

6. A compound of claim 4 wherein $R_1=R_9=OH$, $R_2=CH_2CONH_2$, $R_3$-$R_8$ and $R_{14}$ are all H, and X=S.

7. A compound of claim 4 wherein $R_1=R_9=OH$, $R_2=CH_3CH(OH)$, $R_3$-$R_8$ and $R_{14}$ are all H, and X=S.

8. A compound of claim 4 wherein $R_1=R_9=OH$, $R_2=CH_3$, $R_3$-$R_8$ and $R_{14}$ are all H, and X=S.

9. A compound of claim 4 wherein $R_1=R_9=OH$, $R_2$=p-hydroxyphenylmethyl, $R_3$-$R_8$ and $R_{14}$ are all H, and X=S.

10. A compound of claim 4 wherein $R_1=R_9=OH$, $R_2$=4-histidylmethyl, $R_3$-$R_8$ and $R_{14}$ are all H, and. X=S.

11. A compound of claim 4 wherein $R_1=R_9=OH$, $R_3=CH_2CONH_2$, $R_2$, $R_4$-$R_8$ and $R_{14}$ are all H, and X=S.

12. A compound of claim 4 wherein $R_1=R_9=OH$, $R_3=CH_3CH(OH)$, $R_2$, $R_4$-$R_8$ and $R_{14}$ are all H, and X=S.

13. A compound of claim 4 wherein $R_1=R_9=OH$, $R_3=CH_3$, $R_2$, $R_4$-$R_8$ and $R_{14}$ are all H, and X=S.

14. A compound of claim 4 wherein $R_1=R_9=OH$, $R_3$=p-hydroxyphenylmethyl, $R_2$, $R_4$-$R_8$ and $R_{14}$ are all H, and X=S.

15. A compound of claim 4 wherein $R_1=R_9=OH$, $R_3$=4-histidylmethyl, $R_2$, $R_4$-$R_8$ and $R_{14}$ are all H, and X=S.

16. A compound of claim 4 wherein $R_1=R_9=OH$, $R_2+R_4=(CH_2)3$, $R_3$, $R_5$-$R_8$ and $R_{14}$ are all H, and X=S.

17. A compound of claim 4 wherein $R_1=R_9=OH$, $R_3+R_4=(CH_2)3$, $R_2$, $R_5$-$R_8$ and $R_{14}$ are all H, and X=S.

18. A compound of claim 4 wherein $R_1=R_9=OH$, $R_5=C_2H_5$, $R_2$-$R_4$, $R_6$-$R_8$ and $R_{14}$ are all H, and X=S.

19. A compound of claim 4 wherein $R_1=R_9=OH$, $R_6=C_2H_5$, $R_2$-$R_5$, $R_7$-$R_8$ and $R_{14}$ are all H, and X=S.

20. A compound of claim 4 wherein $R_1=R_9=OH$, $R_5$=n-$C_3H_7$, $R_2$-$R_4$, $R_6$-$R_8$ and $R_{14}$ are all H, and X=S.

21. A compound of claim 4 wherein $R_1=R_9=OH$, $R_6$=n-$C_3H_7$, $R_2$-$R_5$, $R_7$-$R_8$ and $R_{14}$ are all H, and X=S.

22. A compound of claim 4 wherein $R_1=R_9=OH$, $R_5$=phenyl, $R_2$-$R_4$, $R_6$-$R_8$ and $R_{14}$ are all H, and X=S.

23. A compound of claim 4 wherein $R_1=R_9=OH$, $R_6$=phenyl, $R_2$-$R_5$, $R_7$-$R_8$ and $R_{14}$ are all H, and X=S.

24. A compound of claim 4 wherein $R_1=R_9=OH$, $R_5=CH_3$, $R_2$-$R_4$, $R_6$-$R_8$ and $R_{14}$ are all H, and X=S.

25. A compound of claim 4 wherein $R_1=R_9=OH$, $R_6=CH_3$, $R_2$-$R_5$, $R_7$-$R_8$ and $R_{14}$ are all H, and X=S.

26. A compound of claim 4 wherein $R_1$=ethoxy, $R_9=OH$, $R_3=CH_3CH(OH)$-, $R_2$, $R_4$-$R_8$ and $R_{14}$ are all H, and X=S.

27. A compound of claim 4 wherein $R_1=OH$, $R_9=OH$, $R_9$=ethoxy, $R_3=CH_3CH(OH)$-$R_2$, $R_4$-$R_8$ and $R_{14}$ are all H, and X=S.

28. A compound of claim 4 wherein $R_1$=ethoxy, $R_9$=ethoxy, $R_3=CH_3CH(OH)$-, $R_2$, $R_4$-$R_8$ and $R_{14}$ are all H, and X=S.

29. A compound of claim 4 wherein $R_1$=ethoxy, $R_9=OH$, $R_3+R_4=(CH_2)_3$, $R_2$, $R_5$-$R_8$ and $R_{14}$ are all H, and X=S.

30. A compound of claim 4 wherein $R_1$=OH, $R_9$=ethoxy, $R_3+R_4$=$(CH_2)_3$, $R_2$, $R_5$-$R_8$ and $R_{14}$ are all H, and X=S.

31. A compound of claim 4 wherein $R_1$=ethoxy, $R_9$=ethoxy, $R_3+R_4$=$(CH_2)_3$, $R_2$, $R_5$-$R_8$ and $R_{14}$ are all H, and X=S.

32. A compound of claim 4 wherein $R_1$=ethoxy, $R_9$=OH, $R_3$=p-hydroxphenylmethyl, $R_2$, $R_4$-$R_8$ and $R_{14}$ are all H, and X=S.

33. A compound of claim 4 wherein $R_1$=OH, $R_9$=ethoxy, $R_3$=p-hydroxyphenylmethyl, $R_2$, $R_4$-$R_8$ and $R_{14}$ are all H, and X=S.

34. A compound of claim 4 wherein $R_1$=ethoxy, $R_9$=ethoxy, $R_3$=p-hydroxyphenylmethyl, $R_2$, $R_4$-$R_8$ and $R_{14}$ are all H, and X=S.

35. A compound of claim 4 wherein $R_1$=ethoxy, $R_9$=OH, $R_2$-$R_8$ and $R_{14}$ are all H, and X=S.

36. A compound of claim 4 wherein $R_1$=OH, $R_9$=ethoxy, $R_2$-$R_8$ and $R_{14}$ are all H, and X=S.

37. A compound of claim 4 wherein $R_1$=ethoxy, $R_9$=ethoxy, $R_2$-$R_8$ and $R_{14}$ are all H, and X=S.

38. A compound of claim 4 wherein $R_1$=ethoxy, $R_9$=OH, $R_3$=methyl, $R_2$, $R_4$-$R_8$ and $R_{14}$ are all H, and X=S.

39. A compound of claim 4 wherein $R_1$=OH, $R_9$=ethoxy, $R_3$=methyl, $R_2$, $R_4$-$R_8$ and $R_{14}$ are all H, and X=S.

40. A compound of claim 4 wherein $R_1$=ethoxy, $R_9$=ethoxy, $R_3$=methyl, $R_2$, $R_4$-$R_8$ and $R_{14}$ $R_{14}$ are all H, and X=S.

41. A pharmaceutical composition comprising a pharmaceutically acceptable excipient and a compound of the formula:

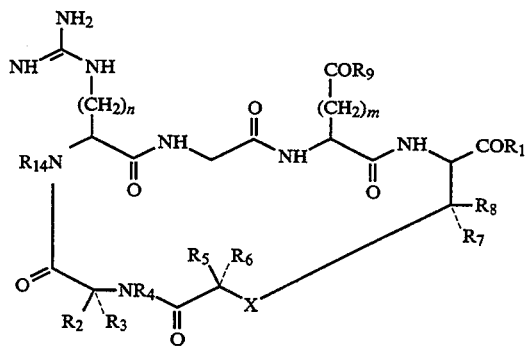

wherein
- $R_1$ and $R_9$ are the same or different and are selected from the group consisting of hydroxy, $C_1$-$C_4$ alkoxy and benzyloxy;
- $R_2$ or $R_3$ is hydrogen and the remaining substituent is selected from the group consisting of hydrogen, $C_1$-$C_6$ alkyl which includes branched alkyl groups, and substituted $C_1$-$C_6$ alkyl where the substituent are selected from the group consisting of amino, hydroxy, mercapto, carboxy, carboxamide, guanidino, phenyl, hydroxyphenyl, indolyl, and imidazolyl;
- $R_5$ or $R_6$ is hydrogen and the remaining substituent is selected from the group consisting of hydrogen, phenyl, $C_1$-$C_6$ alkyl which includes branched alkyl groups, and substituted $C_1$-$C_6$ alkyl where the substituents are selected from the Soup consisting of amino, hydroxy, mercapto, carboxy, carboxamide, guanidino, phenyl, hydroxyphenyl, indolyl, and imidazolyl;
- $R_7$ or $R_8$ is hydrogen or $C_1$-$C_6$ alkyl which includes branched alkyl groups and the remaining substituent is selected from the group consisting of hydrogen, $C_1$-$C_6$ alkyl which includes branched alkyl groups, and substituted $C_1$-$C_6$ alkyl where the substituent is selected from the group consisting of amino, hydroxy, mercapto, carboxy, carboxamide, guanidino, phenyl, hydroxyphenyl, indolyl, and imidazolyl;
- $R_4$ is hydrogen or may be joined with $R_2$ or $R_3$ to form an alkylene bridge of three or four carbon atoms or an alkylene bridge of two carbon atoms and one S heteroatom;
- X is an O or S heteroatom or an S heteroatom bearing one or two O heteroatoms;
- $R_{14}$ is selected from the group consisting of hydrogen, $C_1$-$C_4$-alkyl, $C_6$-$C_{12}$-aryl, and $C_6$-$C_{12}$-aryl-$C_1$-$C_4$-alkyl;
- n is 3;
- m is 1;
- and the pharmaceutically acceptable salts thereof, provided that the chirality of the carbon atoms bearing the $(CH_2)_n$ sidechain and the $(CH_2)_m$ sidechain is S, the chirality of the carbon atom bearing the $COR_1$ group is R, and the chirality of the carbon atom bearing substituents $R_2$ and $R_3$ corresponds to that of a D amino acid.

42. A method for inhibiting platelet aggregation which method comprises administering a platelet aggregation inhibiting amount of a compound of the formula:

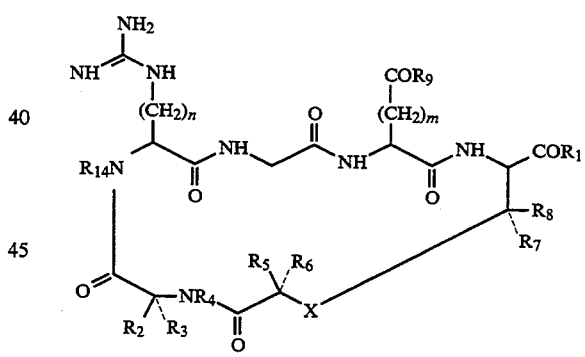

wherein
- $R_1$ and $R_9$ are the same or different and are selected from the group consisting of hydroxy, $C_1$-$C_4$ alkoxy and benzyloxy;
- $R_2$ or $R_3$ is hydrogen and the remaining substituent is selected from the group consisting of hydrogen, $C_1$-$C_6$ alkyl which includes branched alkyl groups, and substituted $C_1$-$C_6$ alkyl where the substituent are selected from the group consisting of amino, hydroxy, mercapto, carboxy, carboxamide, guanidino, phenyl or hydroxyphenyl, indolyl, and imidazolyl;
- $R_5$ or $R_6$ is hydrogen and the remaining substituent is selected from the group consisting of hydrogen, phenyl, $C_1$-$C_6$ alkyl which includes branched alkyl groups, and substituted $C_1$-$C_6$ alkyl where the substituents are selected from the group consisting of amino, hydroxy, mercapto, carboxy, carboxamide, guanidino, phenyl, hydroxphenyl, indolyl, and imidazolyl;

$R_7$ or $R_8$ is hydrogen or $C_1$-$C_6$ alkyl which includes branched alkyl groups and the remaining substituent is selected from the group consisting of hydrogen, $C_1$-$C_6$ alkyl which includes branched alkyl groups, and substituted $C_1$-$C_6$ alkyl where the substituent is selected from the group consisting of amino, hydroxy, mercapto, carboxy, carboxamide, guanidino, phenyl, hydroxyphenyl, indolyl, and imidazolyl;

$R_4$ is hydrogen or may be joined with $R_2$ or $R_3$ to form an alkylene bridge of three or four carbon atoms or an alkylene bridge of two carbon atoms and one S heteroatom;

X is an O or S heteroatom or an S heteroatom bearing one or two O heteroatoms;

$R_{14}$ is selected from the group consisting of hydrogen, $C_1$-$C_4$-alkyl, $C_6$-$C_{12}$-aryl, and $C_6$-$C_{12}$-aryl-$C_1$-$C_4$-alkyl;

n is 3;

m is 1; and the pharmaceutically acceptable salts thereof; provided that the chirality of the carbon atoms bearing the $(CH_2)_n$ sidechain and the $(CH_2)_m$ $l$ sidechain is S, the chirality of the carbon atom bearing the $COR_1$ group is R, and the chirality of the carbon atom bearing substituents $R_2$ and $R_3$ corresponds to that of a D amino acid.

43. A method for reducing platelet aggregation in a mammal, comprising administering a pharmaceutically effective amount of the composition of matter as defined by claim 1 to said mammal.

44. The method of claim 43 further comprising administering said composition of matter to said mammal in admixture with a pharmaceutically acceptable carrier.

45. A method for treating a mammal who has an increased propensity for thrombus formation, comprising administering a pharmaceutiacally effective amount of the composition of matter as defined by claim 1 to said mammal.

46. A composition of matter for reducing platelet aggregation in a mammal, comprising the composition of matter as defined by claim 1.

47. A composition of matter for treating a mammal who has an increased propensity for thrombus formation, comprising the composition of matter as defined by claim 1.

48. A composition of matter for inhibiting fibrinogen binding to platelets in a mammal, comprising the composition of matter as defined by claim 1.

49. A composition of matter comprising the compositions of claim 1 wherein $R_1$ is $C_1$-$C_6$ alkoxy which includes branched and unsaturated alkyl groups.

50. A composition of matter comprising the compositions of claim 1 wherein $R_9$ is $C_1$-$C_6$ alkoxy which includes branched and unsaturated alkyl groups.

51. A composition of matter comprising the compositions of claim 1 wherein $R_1$ and $R_9$ are both $C_1$-$C_6$ alkoxy which includes branched and unsaturated alkyl groups.

52. A method of treating a mammal who has an increased propensity for thrombus formation which comprises administering to said mammal a therapeutically effective amount of the composition of claim 49, 50, or 51 wherein the $R_1$ and $R_9$ alkoxy groups are hydrolyzed following administration to said mammal.

53. A method for treating a mammal who has an increased propensity for thrombus formation, comprising administering a pharmaceutically effective amount of the composition of matter as defined by claim 1 in combination with a thrombolytic agent.

54. A method for treating a mammal who has an increased propensity for thrombus formation, comprising administering a pharmaceutically effective amount of the composition of matter as defined by claim 1 in combination with an anticoagulant.

55. A method for treating a mammal who has an increased propensity for thrombus formation, comprising administering a pharmaceutically effective amount of the composition of matter as defined by claim 1 following angioplasty.

56. A compound of claim 4 wherein $R_1=R_9=OH$, $R_3=$p-hydroxphenylmethyl, $R_2$, $R_4$-$R_8$ and $R_{14}$ are all H, and X=SO.

57. A compound of claim 4 wherein $R_1=R_9=OH$, $R_3=$p-hydroxphenylmethyl, $R_2$, $R_4$-$R_8$ and $R_{14}$ are all H, and X=$CH_2$.

* * * * *